United States Patent
Asztalos et al.

(10) Patent No.: US 9,696,276 B2
(45) Date of Patent: *Jul. 4, 2017

(54) METHODS FOR SEPARATION AND IMMUNO-DETECTION OF BIOMOLECULES, AND APPARATUS RELATED THERETO

(71) Applicant: Boston Heart Diagnostics Corporation, Framingham, MA (US)

(72) Inventors: Bela F. Asztalos, Framingham, MA (US); Ernst J. Schaefer, Natick, MA (US)

(73) Assignee: Boston Heart Diagnostics Corporation, Framingham, MA (US)

( * ) Notice: Subject to any disclaimer, the term of this patent is extended or adjusted under 35 U.S.C. 154(b) by 1084 days.

This patent is subject to a terminal disclaimer.

(21) Appl. No.: 13/896,765

(22) Filed: May 17, 2013

(65) Prior Publication Data

US 2013/0248370 A1    Sep. 26, 2013

Related U.S. Application Data

(63) Continuation of application No. 12/567,737, filed on Sep. 26, 2009, now Pat. No. 8,470,541.

(60) Provisional application No. 61/100,725, filed on Sep. 27, 2008.

(51) Int. Cl.
  *G01N 33/53* (2006.01)
  *G01N 27/447* (2006.01)
  *C12M 1/26* (2006.01)

(52) U.S. Cl.
  CPC ....... *G01N 27/44739* (2013.01); *C12M 33/00* (2013.01)

(58) Field of Classification Search
  None
  See application file for complete search history.

(56) References Cited

U.S. PATENT DOCUMENTS

| | | | |
|---|---|---|---|
| 3,703,591 A | 11/1972 | Bucolo | |
| 4,245,041 A | 1/1981 | Denney | |
| 4,330,299 A | 5/1982 | Cerami | |
| 4,495,279 A | 1/1985 | Karpetsky et al. | |
| 4,683,195 A | 7/1987 | Mullis et al. | |
| 4,683,202 A | 7/1987 | Mullis | |
| 4,800,159 A | 1/1989 | Mullis et al. | |
| 4,999,289 A | 3/1991 | Akiba et al. | |
| 5,223,392 A | 6/1993 | Cohen | |
| 5,360,741 A * | 11/1994 | Hunnell | B01L 7/00 422/136 |
| 5,436,149 A | 7/1995 | Barnes | |
| 5,459,069 A * | 10/1995 | Palsson | C07K 14/5403 435/289.1 |
| 5,843,663 A | 12/1998 | Stanley et al. | |
| 5,849,481 A | 12/1998 | Urdea et al. | |
| 5,849,486 A | 12/1998 | Heller et al. | |
| 5,851,772 A | 12/1998 | Mirzabekov et al. | |
| 5,888,827 A | 3/1999 | Kayahara et al. | |
| 5,900,481 A | 5/1999 | Lough et al. | |
| 5,919,626 A | 7/1999 | Shi et al. | |
| 5,955,351 A * | 9/1999 | Gerdes | B01L 3/502 422/112 |
| 6,080,581 A * | 6/2000 | Anderson | C12M 27/10 435/394 |
| 6,194,164 B1 | 2/2001 | Matsui et al. | |
| 6,316,196 B1 | 11/2001 | Morten | |
| 6,357,516 B1 * | 3/2002 | Judge | F28F 3/083 165/166 |

(Continued)

FOREIGN PATENT DOCUMENTS

EP    1186672 A2    3/2002
EP    1651774 B1    9/2007

(Continued)

OTHER PUBLICATIONS

Gordon, D.J. et al., "High-density Lipoprotein Cholesterol and Cardiovascular Disease. Four Prospective American Studies," Circulation, Jan. 1989; 79(1):8-15.

Asztalos, B.F., et al., "Two-dimensional electrophoresis of plasma lipoproteins: recognition of new apo A-I containing subpopulations," Biochim Biophys Acta., Sep. 8, 1993; 1169(3):291-300.

Asztalos, B.F., et al., "Distribution of ApoA-I-containing HDL Subpopulations in Patients with Coronary Heart Disease," Arterioscler Thromb Vasc Biol., Dec. 2000; 20(12)2670-6.

Asztalos, B.F., et al., "High-density Lipoprotein Subpopulation Profile and Coronary Heart Disease Prevalence in Male Participants of the Framingham Offspring Study," Arterioscler Thromb Vasc Biol., Nov. 2004; 24(11):2181-7.

(Continued)

Primary Examiner — Ann Lam
(74) Attorney, Agent, or Firm — Brown Rudnick LLP; Thomas C. Meyers

(57) ABSTRACT

Disclosed are methods and apparatus for separation of biomolecules via two-dimensional gel electrophoresis, methods and apparatus for immunoblotting separated biomolecules, and methods for the use of biomolecules processed via the methods and apparatus of the present invention, including use in a clinical setting. The methods and apparatus for separation of biomolecules via two-dimensional gel comprises vertical agarose gel electrophoresis in the first dimension, and the electrophoresis of a novel non-denaturing 3-35% concave gradient polyacrylamide gel in the second dimension. This novel gel can be cast in a modified gel caster that can facilitate the pouring of multiple gels simultaneously. The methods and apparatus for immunoblotting are useful with any type of immunoblotting, including Western blot, Northern blot, and Southern blot analyzes. These methods and apparatus provide safe, efficient and cost-effective immunoblots, while facilitating the reduction of exposure to toxic or radioactive materials, as well as the disposal of those materials.

19 Claims, 9 Drawing Sheets

(56) References Cited

U.S. PATENT DOCUMENTS

| | | | |
|---|---|---|---|
| 6,410,309 B1* | 6/2002 | Barbera-Guillem | C12M 23/10 |
| | | | 435/297.5 |
| 6,582,908 B2 | 6/2003 | Fodor et al. | |
| 7,417,039 B2 | 8/2008 | Davis | |
| 7,435,541 B2 | 10/2008 | Olson et al. | |
| 7,608,405 B2 | 10/2009 | Ebinuma et al. | |
| 7,659,107 B2 | 2/2010 | Smith et al. | |
| 7,700,277 B2 | 4/2010 | Ambrose et al. | |
| 7,871,789 B2 | 1/2011 | Yonehara et al. | |
| 8,003,795 B2 | 8/2011 | Liu et al. | |
| 8,026,345 B2 | 9/2011 | Burghardt et al. | |
| 8,093,222 B2 | 1/2012 | Freier et al. | |
| 8,470,541 B1* | 6/2013 | Asztalos | C12M 33/00 |
| | | | 435/7.1 |
| 2003/0143223 A1 | 7/2003 | Cabezas et al. | |
| 2004/0131658 A1 | 7/2004 | Kaput | |
| 2004/0259179 A1 | 12/2004 | Assmann et al. | |
| 2005/0054005 A1 | 3/2005 | Ellis et al. | |
| 2005/0059581 A1 | 3/2005 | Mantzoros | |
| 2005/0281868 A1 | 12/2005 | Lane | |
| 2006/0251625 A1* | 11/2006 | Shisler | A61K 38/162 |
| | | | 424/93.2 |
| 2006/0293225 A1 | 12/2006 | Dialynas et al. | |
| 2007/0003600 A1 | 1/2007 | Moore et al. | |
| 2007/0015291 A1 | 1/2007 | Smith | |
| 2007/0031838 A1 | 2/2007 | Ambrose et al. | |
| 2007/0059722 A1 | 3/2007 | Salonen et al. | |
| 2007/0196841 A1 | 8/2007 | Ruano et al. | |
| 2007/0218519 A1 | 9/2007 | Urdea et al. | |
| 2008/0227210 A1 | 9/2008 | Smith | |
| 2008/0293054 A1 | 11/2008 | Medina et al. | |
| 2008/0300170 A1 | 12/2008 | Gelber et al. | |
| 2009/0197242 A1 | 8/2009 | Kaddurah-Daouk et al. | |
| 2009/0246801 A1 | 10/2009 | Smith | |
| 2010/0063153 A1 | 3/2010 | Chatterjee et al. | |
| 2010/0076787 A1 | 3/2010 | Naylor et al. | |
| 2010/0120136 A1* | 5/2010 | Larsen | C12M 27/10 |
| | | | 435/297.1 |
| 2010/0167306 A1 | 7/2010 | Smith | |
| 2010/0190172 A1 | 7/2010 | Cargill et al. | |
| 2010/0204557 A1 | 8/2010 | Kiaie et al. | |
| 2011/0112186 A1 | 5/2011 | Link et al. | |
| 2011/0250618 A1 | 10/2011 | Nelson et al. | |
| 2011/0269735 A1 | 11/2011 | Shiffman et al. | |
| 2012/0065514 A1 | 3/2012 | Naghavi et al. | |
| 2012/0165206 A1* | 6/2012 | Rosenfeld | G01N 33/5091 |
| | | | 506/9 |

FOREIGN PATENT DOCUMENTS

| | | |
|---|---|---|
| WO | 02/48715 | 6/2002 |
| WO | 2004/050898 A2 | 6/2004 |
| WO | WO-2005/012566 A2 | 2/2005 |
| WO | WO-2006/008656 A2 | 1/2006 |
| WO | WO-2006/072654 A1 | 7/2006 |
| WO | WO-2007/012884 A1 | 2/2007 |
| WO | WO-2007/061995 A2 | 5/2007 |
| WO | 2007/128884 A1 | 11/2007 |
| WO | 2008/131224 A2 | 10/2008 |
| WO | WO-2009/106838 A1 | 9/2009 |
| WO | WO-2011/058232 A1 | 5/2011 |
| WO | 2013/056087 A2 | 4/2013 |
| WO | WO-2013/078122 A1 | 5/2013 |

OTHER PUBLICATIONS

Asztalos, B.F., et al., "Value of High-Density Lipoprotein (HDL) Subpopulations in Predicting Recurrent Cardiovascular Events in the Veterans Affairs HDL Intervention Trial," Arterioscler Thromb Vasc Biol., Oct. 2005; 25(10):2185-2191.

Ahern et al., Biochemical, Reagent Kits Offer Scientists Good Return on Investment, The Science, vol. 9, pp. 1-5, 1995.

Armitage, J., "The safety of statins in clinical practice," Lancet, 2007, pp. 1781-1790, vol. 370.

Assmann G, Kannenberg F, Ramey DR, Musliner TA, Gutkin SW, Veltri EP. Effects of ezetimibe, simvastatin, atorvastatin, and ezetimibe-statin therapies on non-cholesterol sterols in patients with primary hypercholesterolemia. Curr Med Res Opin 2008;24:249-59.

Asztalos B F et al: "LpA-I, LpA-I:A-II HDL and CHD-risk: The Framingham Offspring Study and the Veterans Affairs HDL Intervention Trial", Atherosclerosis, vol. 188, No. 1, Sep. 1, 2006 (Sep. 1, 2006), pp. 59-67, XP028071474, Elsevier Ireland Ltd, Dublin ISSN: 0021-9150, DOI: 10.1016/J.Atherosclerosis.2005.10.018.

Ballantyne CM, Houri J, Notarbartolo A, et al. Effect of ezetimibe coadministered with atorvastatin in 628 patients with primary hypercholesterolemia: a prospective, randomized, double-blind trial. Circulation 2003;107:2409-15.

Ballantyne, C.M., et al., "Risk for myopathy with statin therapy in high-risk patients," Arch Intern Med, 2003, pp. 553-564, vol. 163.

Barrett, J.C., et al., Haploview: analysis and visualization of LD and haplotype maps, Bioinformatics, 2005, pp. 263-265, vol. 21.

Bland et al., "Multiple significance tests: the Bonferroni method," BMJ, vol. 310, p. 170, Jan. 21, 1995.

Burke et al., Mechanisms of the Liebermann-Burchard and Zak Color Reactions for Cholesterol, Clin. Chem .20(7), 794-801, 1974.

Burke, J. P., et al., "Rapid Rise in the Incidence of Type 2 Diabetes From 1987 to 1996," (1999) Arch Intern Med. 159:1450-1456.

Camont et al: "Biological activities of HDL subpopulations and their relevance to cardiovascular disease", Trends in Molecular Medicine, vol. 17, No. 10, Oct. 1, 2011.

Carlton et al., "Functional single nucleotide polymorphism-based association studies," Human Genomics, 2(6): 391-402 (2006).

Catapano AL, Reiner Z, De Backer G, et al. ESC/EAS Guidelines for the management of dyslipidaemias the Task Force for the management of dyslipidaemias of the European Society of Cardiology (ESC) and the European Atherosclerosis Society (EAS). Atherosclerosis 2011;217:3-46.

Cholesterol Treatment Trialists' (CTT) Collaborators, Efficacy and safety of cholesterol-lowering treatment: prospective meta-analysis of data from 90,056 participants in 14randomised trials of statins, Lancet, 2005, pp. 1267-1278, vol. 366.

Corsini, A., et al., "Pharmacokinetic interactions between statins and fibrates," Am J. Cardiol, 2005,pp. 44K-49K, vol. 96.

Couvert P et al, Association between a Frequent Allele of the Gene Encoding OATP1B1 and the Enhanced LDL-Lowering Response to Fluvastatin Therapy, Pharmacogenomics 9: 1217-1227, 2008.

Cuyper et al., Determination of changes in serum lathosterol during treatment with simvastatin to evaluate the role of lathosterol as a parameter for whole body cholesterol synthesis. Clin Chim Acta 1993;219:123-30.

Davidson MH, Ballantyne CM, Kerzner B, et al. Efficacy and safety of ezetimibe coadministered with statins: randomised, placebo-controlled, blinded experience in 2382 patients with primary hypercholesterolemia. Int J Clin Pract 2004;58:746-55.

Davidson MH, McGarry T, Bettis R, et al. Ezetimibe coadministered with simvastatin in patients with primary hypercholesterolemia. J Am Coll Cardiol 2002;40:2125-34.

Davis, H et al. Zetia: Inhibition of Niemann-Pick C1 Like 1 (NPC1L1) to Reduce Intestinal Cholesterol Absorption and Treat Hyperlipidemia. Journal of Atherosclerosis and Thrombosis. May 2007, vol. 14; pp. 99-108.

De Cuyper I, Wolthers BG, van Doormaal JJ, Wijnandts PN. Determination of changes in serum lathosterol during treatment with simvastatin to evaluate the role of lathosterol as a parameter for whole body cholesterol synthesis. Clin Chim Acta 1993;219:123-30.

Deepak Voora et al., The SLCO1B18*5 Genetic Variant is Associated with Statin-Induced Side Effects, Journal of the American College of Cardiology, vol. 54, No. 17, 2009, pp. 1609-1616.

Devlin, B., et al., "Genomic control for association studies," Biometrics, 1999, pp. 997-1004, vol. 55.

Dullaart RPF et al, The Serum Lathosterol to Cholesterol Ratio, an Index of Cholesterol Synthesis,is Not Elevated in Patients With Glomerular Proteinuria and Is Not Associated With Improvement of Hyperlipidemia in Response to Antiproteinuric Treatment, Metabolism 45: 723-730, 1996.

(56) References Cited

OTHER PUBLICATIONS

Espy et al (2006) Clin Microbiol Rev. Jan. 2006; 19(1): 165-256.
Farnier, M et al. Lipid-Altering Eficacy of Ezetimibe/Simvastatin 10/20 mg Compared With Rosuvastatin 10 mg in High-Risk Hypercholesterolaemic Patients Inadequately Controlled With Prior Statin Monotherapy—The In-Cross Study. The International Journal of Clinical Practice. Apr. 2009, vol. 63; pp. 547-559.
Fiegenbaum et al., "The role of common variants of ABCB1, CYP3A4, and CYP3A5 genes in lipidlowering efficacy and safety of simvastatin treatment," Clin. Pharmocol. Ther., vol. 78, pp. 551-558, 2005.
Friedewald WT, Levy RI, Fredrickson DS. Estimation of the concentration of low-density lipoprotein cholesterol in plasma, without use of the preparative ultracentrifuge. Clin Chem 1972;18:499-502.
Frudakis et al., "CYP2D6*4 polymorphism is associated with statin-induced muscle effects,"Pharmacogenetics and Genomics, vol. 17, pp. 695-707, 2007.
Gagne C, Gaudet D, Bruckert E. Efficacy and safety of ezetimibe coadministered with atorvastatin or simvastatin in patients with homozygous familial hypercholesterolemia. Circulation 2002;105:2469-75.
Gazi IF et al, Effect of Ezetimibe in Patients Who cannot Tolerate Statins or cannot Get to the Low Density Lipoprotein Cholesterol Target Despite Taking a Statin, Crur Med Res Opin 23: 2183-2192, 2007.
Generaux GT et al, Impact of SLCOIB1 (OATP1B1) and ABCG2 (BCRP) Genetic Polymorphisms and Inhibition on LDL-C Lowering and Myopathy of Statins, Xenobiot 41: 639-651, 2011.
Goh et al., HPLC analysis of desmosterol, 7-dehydrocholesterol, and cholesterol. Lipids 24.7 (1989): 652-655.
Gouni et al. Effects of ezetimibe and/or simvastatin on LDL receptor protein expression and on LDL receptor and HMG-CoA reductase gene expression: a randomized trial in healthy men. Atherosclerosis 2008;198:198-207.
Grundy et al. Implications of recent clinical trials for the National Cholesterol Education Program Adult Treatment Panel III guidelines. Circulation 2004;110:227-39.
Grundy et al., "Plasma Non-Cholesterol Sterols as Indicators of Cholesterol Absorption." Journal of lipid research (2013) V54 873-875.
Gunderson, K.L., et al., "Whole-genome genotyping of haplotype tag single nucleotide polymorphisms," Pharmacogenomics, 2006, pp. 641-648, vol. 7.
Havekes LM et al. A rapid micro method for apolipoprotein E phenotyping directly in serum. J Lipid Res (1987) 28:455-63.
Heart Protection Study Collaborative Group, "MRC/BHF Heart Protection Study of cholesterol lowering with simvastatin in 20,536 high-risk individuals: a randomised placebo-controlled trial," Lancet, 2002, pp. 7-22, vol. 360.
Hermann et al., "Pharmacokinetics and Drug Disposition: Exposure of atorvastatin is unchangedbut lactone and acid metabolites are increased several-fold in patients with atorvastatin-induced myopathy," Clinical Pharmacology & Therapeutics, vol. 79, No. 6, pp. 532-539, 2006.
Himbergen et al., Comparison of the effects of maximal dose atorvastatin and rosuvastatin therapy on cholesterol synthesis and absorption markers. J Lipid Res 2009;50:730-9.
Hironobu Akao et al., Genetic Variation at the SLC01B1 Gene Locus and Low Density Lipoprotein Cholesterol Lowering Response to Pravastatin in the Elderly, Atherosclerosis, 220, 2012, pp. 413-417.
Ho et al., "Drug and Bile Acid Transporters in Rosuvastatin Hepatic Uptake: Function, Expression, and Pharmacogenetics," Gastroenterology, 130(6): 1793-1806 (2006).
Hsiang et al., "A Novel Human Hepatic Organic Anion Transporting Polypeptide (OATP2): Identification of a liver-specific human organic anion transporting polypeptide and identification of rat and human hydroxymethylglutaryl-CoA reductase inhibitor transporters," J. Biol. Chem., 274(52): 37161-37168 (1999).
International Hapmap Consortium, "A haplotype map of the human genome," Nature, 2005,pp. 1299-1320, vol. 437.
International Search Report for PCT/GB2009/000547, May 11, 2009, 4 pages.
International Search Report and Written Opinion for PCT/US12/60014, dated Apr. 5, 2013, 9 pages.
International Search Report and Written Opinion for PCT/US2013/066860 mailed Jan. 20, 2014, 14 pages.
International Search Report and Written Opinion for PCT/US2013/62241 mailed Jan. 17, 2014, 16 pages.
Isbell et al: "Reproducibility and Reliability of Atherosclerotic Plaque Volume Measurements in Peripheral Arterial Disease with Cardiovascular Magnetic Resonance", Journal of Cardiovascular Magnetic Resonance, vol. 9, No. 1, Jan. 1, 2007, p. 1-15.
Jakulj et al. Baseline cholesterol absorption and the response to ezetimibe/simvastatin therapy: a post-hoc analysis of the Enhance trial. J Lipid Res 2010;51:755-62.
Jones et al. Comparison of the efficacy and safety of rosuvastatin versus atorvastatin, simvastatin, and pravastatin across doses (Stellar* Trial). Am J Cardiol 2003;92:152-60.
Juraschek et al., Alternative Markers of Hyperglycemia and Risk of Diabetes, vol. 35 No. 11, Aug. 8, 2012, p. 1-6.
Kajinami, K., et al., "CYP3A4 genotypes and plasma lipoprotein levels before and after treatment with atorvastatin in primary hypercholesterolemia," Am J Cardiol, 2004, pp. 104-107, vol. 93.
Kameyama et al., "Functional characterization of SLC01B1 (OATP-C) variants, SLC01B1*5,SLC01B1*15 and SCL01B1*15+C1007G, by using transient expression systems of HeLa and HEK293 cells," Pharmacogenetics and Genomics, vol. 15, No. 7, pp. 513-522. Jul. 2005.
Kim et. al., "3-Hydroxy-3-methylglutaryl-coenzyme A reductase inhibitors (statins) and genetic variability(single nucleotide polymorphisms) in a hepatic drug uptake transporter: What's it all about?," Clinical Pharmacology & Therapeutics, vol. 75, No. 5, pp. 381-385, 2004.
Kim, K.T., et al., "Increased systemic exposure to rosuvastatin in Asian subjects residing in the United States compared to Caucasian subjects," Clinical Pharmacology and Therapeutics, 2008, p. S 14,vol. 83.
Kivisto et al., "Influence of Drug Transporter Polymorphisms on Pravastatin Pharmacokinetics in Humans," Pharmceutical Research, vol. 24, No. 2, pp. 239-247, Feb. 2007.
Kolberg, J. A., et al., "Development of a Type 2 Diabetes Risk Model From a Panel of Serum Biomarkers From the Inter99 Cohort," (2009) Diabetes Care 32(7):1207-12.
Konig, J., et al., Pharmacogenomics of human OATP transporters, Naunyn Schmiedebergs Arch Pharmacol2006, pp. 432-443, vol. 372.
Lakoski SG, Xu F, Vega GL, et al. Indices of Cholesterol Metabolism and Relative Responsiveness to Ezetimibe and Simvastatin. J Clin Endocrinol Metab 2010;95:800-9.
Lamon-Fava S, Diffenderfer MR, Barrett PH, et al. Effects of different doses of atorvastatin on human apolipoprotein B-100, B-48, and A-I metabolism. J Lipid Res 2007;48:1746-53.
Law, M., et al., "Statin safety: a systematic review," Am J. Cardiol, 2006, pp. S52-S60, vol. 97.
Link et al., "SLC01B1 Variants and Statin-Induced Myopathy—A Genomewide Study," N. Engl. J. Med., 359: 789-799 (2008).
Lund, E., et al. "Determination of serum levels of unesterified lathosterol by isotope dilution-mass spectrometry." Scandinavian journal of clinical & laboratory investigation 49.2 (1989): 165-171.
Luzón-Toro et al., "Gas chromatographic-mass spectrometric determination of brain levels of α-cholest-8-en-3β-ol (lathosterol)." Journal of Chromatography B 850.1 (2007): 177-182.
Mangravite, L.M., et al., "Clinical implications of pharmacogenomics of statin treatment,"Pharmacogenomics J, 2006, pp. 360-374, vol. 6.
Mann, D. M., et al., "The Multi-Ethnic Study of Atherosclerosis," (MESA) (2010) Am J Epidemiol 171(9):980-988. Jan. 2010.
Matthan NR et al., Impact of simvastatin, niacin, and/or antioxidants on cholesterol metabolism in CAD patients with low HDL. J Lipid Res. 2003;44:800-806.

(56) References Cited

OTHER PUBLICATIONS

Matthan NR et al., "Deuterium uptake and plasma cholesterol precursor levels correspond as methods for measurement of endogenous cholesterol synthesis in hypercholesterolemic women.", Lipids. 2000;35:1037-1044.
Matthan, N et al. Cholesterol Absorption and Synthesis Markers in Individuals With and Without a CHD Event During Pravastatin Therapy: Insights From the Prosper Trial. Journal of Lipid Research. Jul. 3, 2009, vol. 51; pp. 202-209.
Miettinen et al., Serum plant sterols and cholesterol precursors reflect cholesterol absorption and synthesis in volunteers of a randomly selected male population. Am J Epidemiol 1990;131:20-31.
Miettinen TA, Gylling H, Lindbohm N, Miettinen TE, Rajaratnam RA, Relas H. Serum noncholesterol sterols during inhibition of cholesterol synthesis by statins. J Lab Clin Med 2003;141:131-7.
Miettinen TA, Strandberg TE, Gylling H. Noncholesterol sterols and cholesterol lowering by long-term simvastatin treatment in coronary patients: relation to basal serum cholestanol. Arterioscler Thromb Vasc Biol 2000;20:1340-6.
Mikko Niemi et al., Organic Anion Transporting Polypeptide 1B1: a Genetically PolymorphicTransporter of Major Impotance for Hepatic Drug Uptake, Pharmacological Reviews, vol. 63, No. 1, 2011, pp. 157-181.
Molden, E., "Variability in Cytochrome P450-Mediated Metabolism of Cardiovascular Drugs: Clinical Implications and Practical Attempts to Avoid Potential Problems," Heart Drug, 2004, pp. 55-79, vol. 4.
Morimoto et al., "Candidate gene approach for the study of genetic factors involved in HMG-CoA reductase inhibitor-induced rhabdomyolysis," Eighteenth JSSX Annual Meeting, 8PE-32 (2003).
Morimoto et al; A Novel Variant Allele of OATP-C (SLC01B1) Found in a Japan Patient with Pravastatin-induced Myopathy, Drug Metab. Pharmocokinet. vol. 19, pp. 453-455; 2004.
Morimoto, K, et al., "OATP-C(OATP01B1)*15 is associated with statin-induced myopathy in hypercholesterolemia patients," Clinical Pharmacology & Therapeutics, 2005, pp. P21-P21 vol. 77.
Morrone D, Weintraub WS, Toth PP, Hanson ME, Lowe RS, Lin J, Shah AK, and Tershakovec AM. Lipid-altering efficacy of ezetimibe plus statin and statin monotherapy and identification of factors associated with treatment response: A pooled analysis of over 21,000 subjects from 27 clinical trials. Atherosclerosis , in press. 2012.223, 251-261.
Mulder et al., "Association of polymorphism in the cytochrome CYP2D6 and the efficacy and tolerability of simvastatin," Clin. Pharmacol. Ther., vol. 70, pp. 546-551, 2001.
Márk, L et al., Change in the cholesterol metabolism associated with the combined inhibition of synthesis and absorption. Orvosi hetilap 148.14 (2007): 627.
Nauck et al., Clinical Chemistry Feb. 2002 vol. 48 No. 2 236-254.
Niemi et al., "Acute effects of pravastatin on cholesterol synthesis are associated with SLC01B1(encoding OATP1B1) haplotype *17," Pharmacogenet. Genomics, vol. 15, No. 5, pp. 303-309, May 15, 2005.
Niemi et al., "High plasma pravastatin concentrations are associated with single nucleotide polymorphisms and haplotypes of organic anion transporting polypeptide-C (OATP-C, SCL01B1)," Pharmacogenetics, 14: 429-440 (2004).
Nishizato et al., "Polymorphisms of OATP-C (SLC21A6) and OAT3 (SLC22A8) genes: Consequences for pravastatin pharmacokinetics," Clin. Pharmacol. Ther., 73(6): 554-565 (2003).
Nissinen et. al., Applicability of non-cholesterol sterols in predicting response in cholesterol metabolism to simvastatin and fluvastatin treatment among hypercholesterolemic men. Nutr Metab Cardiovasc Dis 2010;20:308-16.
Nozawa et al.,"Genetic Polymorphisms of Human Organic Anion Transporters OATP-C(SLC21A6) and OATP-B (SLC21A9): Allele Frequiences in the Japanese Population and Functional Analysis," The Journal of Pharmacology and Experimental Therapeutics, vol. 302, No. 2, pp. 2002.
Oh, J., et al., "Genetic determinants of statin intolerance," Lipids Health Dis, 2007, pp. 6:7.
Ooi et. al., Dose-dependent effect of rosuvastatin on apolipoprotein B-100 kinetics in the metabolic syndrome. Atherosclerosis 2008;197:139-46.
Ordovas JM et al, The APOE Locus and the Pharmacogenetics of Lipid Response, Cur Opin Lipidol 13: 113-117, 2002.
Pasanen et al., "Different Effects of SLC01B1 Polymorphism on the Pharmacokinetics of Atorvastatin and Rosuvastatin," Clin. Pharmacol. Ther., 82(6): 726-733 (2007).
Pasanen et al., "Global analysis of genetic variation in SLC01B1," Pharmacogenomics, vol. 9, No. 1, pp. 19-33, Jan. 2008.
Pasanen et al.,"SLC01B1 polymorphism markedly affects the pharmacokinetics of simvastatinacid," Pharmacogenet. Genomics, vol. 16, No. 12, pp. 873-879, Dec. 2006.
Pasanen et al.; Frequencies of single nucleotide polymorphisms and haplotypes of organic anion transporting polypeptide 1B1 SLCO1B1 gene in a Finnish population, Eur. J, Clin. pharmacol. vol. 62, pp. 409-415; 2006.
Pearson et al. Effectiveness of ezetimibe added to ongoing statin therapy in modifying lipid profiles and low-density lipoprotein cholesterol goal attainment in patients of different races and ethnicities: a substudy of the Ezetimibe add-on to statin for effectiveness trial. Mayo Clin Proc 2006;81:1177-85.
Pearson et. al., A community-based, randomized trial of ezetimibe added to statin therapy to attain NCEP ATP III goals for LDL cholesterol in hypercholesterolemic patients: the ezetimibe add-on to statin for effectiveness (EASE) trial. Mayo Clin Proc 2005;80:587-95.
Perk et al. European Guidelines on cardiovascular disease prevention in clinical practice (version 2012): The Fifth Joint Task Force of the European Society of Cardiology and Other Societies on Cardiovascular Disease Prevention in Clinical Practice Cardiovascular Prevention & Rehabilitation, Eur Heart J 2012;33:1635-701.
Price, A.L., et al., "Principal components analysis corrects for stratification in genome-wide association studies," Nat Genet, 2006, pp. 904-909, vol. 38.
Purcell, S., et al., "PLINK: a tool set for whole-genome association and population-based linkage analyses," Am J Hum Genet, 2007, pp. 559-575, vol. 81.
R Development Core Team, "R: A Language and Environment for Statistical Computing," Vienna, Austria: R Foundation for Statistical Computing, 2007.
Reihnér E, Rudling M, Ståhlberg D, et al. Influence of pravastatin, a specific inhibitor of HMG-CoA reductase, on hepatic metabolism of cholesterol. N Engl J Med 1990;323:224-8.
Robinson, "Simvastatin: present and future perspectives," Expert Opin. Pharmacother., 8(13): 2159-2172 (2007).
Romaine SPR et al, The Influence of SLC01B1 (OATP1B1) Gene Polymorphisms on Response to Statin Therapy,Pharmacogenom J 10: 1-11, 2010.
Ruano et al., Physiogenomic Association of Statin-Related Myalgia to Serotonin Receptors, Muscle Nerve, vol. 36, pp. 329-335, 2007.
Schaffer, R., et al. "Comparison of two isotope dilution/mass spectrometric methods for determination of total serum cholesterol." Clinical chemistry 28.1 (1982): 5-8.
Schmidt, M. I., et al., "The Atherosclerosis Risk in Communities study," (2005) Diabetes Care 28(8):2013-2018.
Search Study Collaborative Group, "Study of the effectiveness of additional reductions in cholesterol and homocysteine (Search): characteristics of a randomized trial among 12064 myocardial infarction survivors," Am Heart J, 2007, pp. 815-823, vol. 154, No. e6.
Shitara et al., "Pharmacokinetic and pharmacodynamic alterations of 3-hydroxy-3-methylglutaryl coenzyme A (HMG-CoA) reductase inhibitors: drug-drug interactions and interindividual differences in transporter and metabolic enzyme functions," Pharmacol Ther, 2006, pp. 71-105, vol. 112.

(56) References Cited

OTHER PUBLICATIONS

Simonson, S.G., et al., "Rosuvastatin pharmacokinetics in heart transplant recipients administered an antirejection regimen including cyclosporine," Clin Pharmacol Ther, 2004, pp. 167-177, vol. 76.
Stern, M. P., et al., Predicting Diabetes, "Moving Beyond Impaired Glucose Tolerance," (1993) Diabetes 42:706-714.
Stern, M. P., et al., The San Antonio Heart Study, "Sex Difference in the Effects of Sociocultural Status on Diabetes and Cardiovascular Risk Factors in Mexican Americans," (1984) Am. J. Epidemiol. 120(6):834-851.
Streiner et al., "Correction for Multiple Testing, Is there a resolution?," Chest, vol. 140, No. 1, pp. 16-18, Jul. 2011.
Sudhop T, Lutjohann D, Kodal A, et al. Inhibition of intestinal cholesterol absorption by ezetimibe in humans. Circulation 2002;106:1943-8.
Sugiuchi et al., Clinical Chemistry 44:3 522-531 (1998).
The Search Collaborative Group, The New England Journal of Medicine, SLC01B1 Variants and Statin-Induced Myopathy—A Genomewide Study, vol. 359, No. 8, Aug. 21, 2008, pp. 789-799.
Third Report of the National Cholesterol Education Program (NCEP) Expert Panel on Detection, Evaluation, and Treatment of High Blood Cholesterol in Adults (Adult Treatment Panel III) final report. Circulation 2002;106:3143-421.
Thompson, P.D., et al., "Statin-associated myopathy," JAMA, 2003, pp. 1681-1690, vol. 289.
Thongtang et al., "Effects of ezetimibe added to statin therapy on markers of cholesterol absorption and synthesis and LDL-C lowering in hyperlipidemic patients," Atherosclerosis, vol. 225, Issue 2, Dec. 2012, pp. 388-396.
Tirona, R.G., et al., "Polymorphisms in OATP-C: identification of multiple allelic variants associated with altered transport activity among European- and African-Americans," J Biol Chem, 2001, pp. 35669-35675, vol. 276.
Tobert, "Lovastatin and Beyond: The History of the HMG-CoA Reductase Inhibitors," Nat. Rev. Drug Discov., 2(7): 517-526 (2003).
Tyburczy et al., "Evaluation of low trans-fat edible oils by attenuated total reflection-Fourier transform infrared spectroscopy and gas chromatography: a comparison of analytical approaches." Analytical and bioanalytical chemistry 404.3 (2012): 809-819.
United Kingdom Search Report issued in application No. GB0803833.3 on Jun. 27, 2008.
Uusitupa MIJ et al, Lathosterol and Other Noncholesterol Sterols During Treatment of Hypercholesterolemia With Lovastatin Alone and With Cholestyramine or Guar Gum, Arterioscler Thromb 12: 807-813, 1992.
van Himbergen TM, Matthan NR, Resteghini NA, et al. Comparison of the effects of maximal dose atorvastatin and rosuvastatin therapy on cholesterol synthesis and absorption markers. J Lipid Res 2009;50:730-9.
Vanhanen H, Miettinen TA. Pravastatin and lovastatin similarly reduce serum cholesterol and its precursor levels in familiar hypercholesterolaemia. Eur J Clin Pharmacol 1992;42:127-30.
Vladutiu, et al., "Genetic risk factors associated with lipid-lowering drug-induced myopathies, Muscle Nerve," 2006, pp. 153-162, vol. 34.
Warnick et al., Clinical Chemistry Sep. 2001 vol. 47 No. 9 1579-1596.
Wellcome Trust Case Control Consortium, "Genome-wide association study of 14,000 cases of seven common diseases and 3,000 shared controls," Nature, 2007, pp. 661-678, vol. 447.
Weng et al., A systematic review and meta-analysis on the therapeutic equivalence of statins. J Clin Pharm Ther 2010;35:139-51.
Wilson, P. W. F., et al., The Framingham Offspring Study, "Prediction of Incident Diabetes Mellitus in Middle-aged Adults," (2007) Arch Intern Med. 167(10):1068-1074.
Xu et al., "Organic anion transporting polypeptide-1B1 haplotypes in Chinese patients," Acta Pharmacologica Sinica, vol. 28, No. 10, pp. 1693-1697, Oct. 28, 2007.
Zocor datasheet, 2007.httD://www.emc.medicines.ora.uk/emc/assets/c/htmllDisDlavDoc.asD?DocumentID=120.
Zuccaro et al.t "Tolerability of statins is not linked to CYP450 polymorphisms, but reduced CYP2D6 metabolism improves cholesteraemic response to simvastatin and fluvastatin,"Pharmacological Research, vol. 55, pp. 310-317, 2007.
International Search Report and Written Opinion for PCT/US2014/048022, with an International filing date of Jul. 24, 2014, and a mailing date of Feb. 18, 2015, (17 pages).
Miettinen et al., 2000, Noncholesterol Sterols and Cholesterol Lowering by Long-Term Simvastatin Treatment in Coronary Patients: Relation to Basal Serum Cholestanol, Arteriosclerosis, Thrombosis, and Vascular Biology 20(3):1340-1346.
Thompson et al., 2002, Why some patients respond poorly to statins and how this might be remedied, European Heart Journal 23(3):200-206.
Thongtang et al, 2012, Effects of ezetimibe added to statin therapy on markers of cholesterol absorption and synthesis and LCL-C lowering in hyperlipidemic patients, Atherosclerosis 225(2):388:396.
Anderson, 2010, The Clinical Plasma Proteome: A Survey of Clinical Assays for Proteins in Plasma and Serum, Clinica Chemistry 56(2):177-185.
Brambilla et al., 2011, Normal Fasting Plasma Glucose and Risk of Type 2 Diabetes, Diabetes Care 34:1372-1374.
Cruz et al., 2004, Low Adiponectin Levels Predict Type 2 Diabetes in Mexican Children, Diabetes Care 27(6):1451-1453.
Degn et al., 2004, One Week's Treatment With the Long-Acting Glucagon-Like Peptide 1 Derivative Liraglutide (NN2211) Markedly Improves 24-h Glycemia and-and-Cell Function and Reduces Endogenous Glucose Release in Patients with Type 2 Diabetes, Diabetes 53:1187-1194.
Eddy et al., 2003, A trial-validated model of diabetes, Diabetes Care 26(11):3093-3101.
Eddy et al., 2003, Validation of the Archimedes Diabetes Model, Diabetes Care 26(11):3102-3110.
Fumeron et al., 2004, Adiponectin Gene Polymorphisms and Adiponectin Levels Are Independently Associated With the Development of Hyperglycemia During a 3-Year Period; The Epidemiologic Data on the Insulin Resistance Syndrome Prospective Study, Diabetes 53:1150-1157.
Harder et al., 2004, The Effect of Liraglutide, a Long-Acting Glucagon-Like Peptide 1 Derivative, on Glycemic Control, Body Composition, and 24-h Energy Expenditure in Patients; With Type 2 Diabetes, Diabetes Care 27(8):1915-1921.
Kaput et al., 2004, Nutritional genomics: the next frontier in the postgenomic era, Physiol Genomics 16:166-177.
Kaput et al., 2007, Application of nutrigenomic concepts to Type 2 diabetes mellitus, Nutrition, Metabolism & Cardiovascular Diseases 17:89-103.
Kaput, 2004, Diet-Disease Gene Interactions, Nutrition 20:26-31.
Krakoff et al. 2003, Inflammatory Markers, Adiponectin, and Risk of Type 2 Diabetes in the Pima Indian, Diabetes Care 26(6):1745-1751.
Lindstrom et al., 2003, The Diabetes Risk Score, Diabetes Care 26(3):725-731.
Lyssenko et al., 2005, Genetic Prediction of Future Type 2 Diabetes, PLoS Medicine 2(12):e345.
Madsbad et al., 2004, Improved Glycemic Control With No Weight Increase in Patients With Type 2 Diabetes After Once-Daily Treatment With the Long-Acting Glucagon-Like Peptide 1 Analog Liraglutide (NN2211), Diabetes Care 27(6):1335-1342.
Patent Examination Report No. 1 date of issue Jun. 11, 2014 for Patent Application No. AU 2011/261480.
Pradhan et al., 2001, C-Reactive Protein, Interleukin 6, and Risk of Developing Type 2 Diabetes Mellitus, JAMA 286(3):327-334.
Programme for the Prevention of Type 2 Diabetes in Finland, Finnish Diabetes Association, 2003-2010, Published 2003.
Ravussin, 2002, Adiponectin enhances insulin action by decreasing ectopic fat deposition, The Pharmacogenomics Journal 2:4-7.
Spranger et al., Adiponectin and protection against type 2 diabetes mellitus, Lancet 361:226-228 (2003).

(56) References Cited

OTHER PUBLICATIONS

Sturis et al., 2003, GLP-1 derivative liraglutide in rats with b-cell deficiencies: influence of metabolic state on b-cell mass dynamics, British Journal of Pharmacology 140:123-132.

Wilson et al., 2007, Prediction of Incident Diabetes Mellitus in Middle-aged Adults, Arch Intern Med 167:1068-1074.

Schaefer et al., Association of Statin Potency with Markers of Cholesterol Absorption/Synthesis and LDL-C Lowering Efficacy of Ezetimibe Add on Therapy, J of Clinical Lipidology 6(3)286 abstract 160, Jun. 2012.

\* cited by examiner

METHODS FOR SEPARATION AND IMMUNO-DETECTION OF BIOMOLECULES, AND APPARATUS RELATED THERETO

REFERENCE TO RELATED APPLICATIONS

The present application is a continuation of U.S. non-provisional application Ser. No. 12/567,737, filed on Sep. 26, 2009, which claims the benefit of and priority to U.S. provisional patent application Ser. No. 61/100,725, filed on Sep. 27, 2008. The entirety of each application is incorporated by reference herein.

TECHNICAL FIELD

The present invention relates generally to separation and immuno-detection of biomolecules. Specifically, the present invention pertains to methods and apparatus for separation of biomolecules via two-dimensional gel electrophoresis, methods and apparatus for immunoblotting of separated biomolecules, and method for the use of biomolecules processed via the methods and apparatus of the present invention, particularly in a clinical setting.

BACKGROUND

Cardiovascular disease, which includes coronary heart disease (CHD) and stroke, is the leading cause of death and disability in developed countries of the world. CVD is caused by the clogging of arteries. Major accepted risk factors for CVD include age, gender, hypertension, smoking, diabetes, elevated blood low density lipoprotein cholesterol (LDL-C), and decreased blood high density lipoprotein cholesterol (HDL-C).

HDL can protect against atherosclerosis in several ways. The most cited HDL function to protect against atherosclerosis is its participation in reverse cholesterol transport. During this process, HDL removes cholesterol from macrophages in the vessel wall, preventing the transformation of macrophages into foam cells, thereby preventing the build-up of fatty streaks and plaque in the vessel wall. The cholesterol that originated in the macrophages is then carried by HDL to the liver for ultimate excretion into the bile. HDL has additional attributes, including having anti-oxidant, anti-inflammatory, and anti-trhombic capabilities.

HDL can be measured by its cholesterol, total protein, or apoA-I levels. All of these HDL building constituents are distributed in various HDL particles of different size, lipid and protein composition, and surface charge. They also have different pathophysiological relevance. The many different functions of HDL are a result of the presence of specific lipids, proteins, and ratios of the two, as the specific lipids and proteins are unevenly distributed amongst the various HDL subclasses. Cells have several ways of controlling cholesterol level. A cell can use HDL for cholesterol uptake or cholesterol removal depending on the cell lipid level and on HDL lipid and protein composition. The different HDL particles interact with the different cellular-cholesterol removal pathways in a HDL subclass-specific way. The different HDL particles also participate differently in the anti-oxidation and anti-inflammation responses and other HDL functions depending on their size and lipid and protein composition.

Several methods have been developed for separating HDL subclasses in the last half century. Among these methods, two-dimensional gel electrophoresis has the highest resolution and creates the least number of artifacts. The two-dimensional gel-electrophoresis method, first published by C. Fielding in 1987, is commonly used to analyze proteins, as well as other molecules, such as nucleic acids. The analysis involves the separation of mixtures of biomolecules on the basis of two properties (e.g., charge and size) in two dimensions on two-dimensional gels. The two-dimensional gel electrophoresis method for HDL particle separation is based on the combination of two principles of electrophoretic separation: in the first dimension, the lipoprotein particles are separated by electrophoretic charge of HDL particles on agarose gel; in the second dimension, particles are further separated by size (based on molecular weight or lipoprotein-complex mass) on non-denaturing polyacrylamide gel Generally, the separated protein components are detected in the gel as discrete and uniquely positioned spots, recognized initially by monospecific first antibody against the protein of interest and followed by recognition of the first antibody with a second antibody monospecific to the first antibody and labeled with any of a variety of radio labels (such as fluorescent label chemiluminescent labels). Depending on the labeling, this method is specific and can be quantitative by virtue of the utilization of protein immuno-localization and image-analysis. As a result of employing the two-dimensional HDL separation method, different HDL particles have been associated with CVD risk in population-based cross-sectional studies and in drug intervention studies.

The two-dimensional gel electrophoresis technology is also useful in the diagnosis of the homozygous and heterozygous state for rare inherited HDL disorders, such as apoA-I/C-III/A-IV, apoA-I/C-III deficiency, isolated apoA-I deficiency, ABCA1 deficiency, LCAT deficiency, SRB1 deficiency, CETP deficiency, lipoprotein lipase deficiency, hepatic lipase deficiency, and endothelial lipase deficiency. Based on the scans generated using this technique, it has become possible to differentiate among the various HDL-subpopulation profiles and this also allows for very precise evaluation of the severity of CVD-risk in patients. Most of the patients who are carriers of one normal and one damaged gene (referred to as heterozygotes) of the above list also have reduced levels of HDL and premature CVD. Patients who are carriers of two damaged genes (referred to as homozygotes) of the above list generally have a very high risk for premature CHD. Patients affected with apoA-I deficiency have no HDL and have strikingly premature CHD. Whereas, patients affected with LCAT deficiency have only preβ-1 and α-4 HDL particles and are at moderate to high risk for CVD. Different mutations in the cholesterol ester transfer protein (CETP) can cause either increased or decreased CETP activity resulting in different changes in HDL particles. High CETP activity results in low levels of large α-1 and high levels of the small preβ-1 HDL particles. High CETP activity is associated with significant increased risk for CVD. Low CETP activity, which may be due to mutations in the gene encoding CETP or to effects of various drugs, causes high levels of α-1 HDL and low levels of preβ-1 HDL. This HDL subpopulation profile (high α-1 and low preβ-1) is associated with protection against CVD. Various mutations in the genes encoding lipoprotein-, hepatic-, and secretory-phospholipases can also be detected and recognized by their specific HDL subpopulation profile using this method.

Similar to HDL, LDL can also be separated into particles having different sizes; LDL is most commonly separated into small dense (sd) LDL and large LDL particles. It is proven and widely accepted in the lipoprotein field that sdLDL-C is more atherogenic than large LDL-C. The most common method for separating LDL by size is electrophoresis. The quantification of different LDL fractions is based on lipid staining in the gel, followed by density scanning, and then integrating the area under the curve. The major disadvantages of this method are that it is labor and time consuming, and it has poor resolution. A more recent method involves the use of a specific mixture of detergents for removing other lipoproteins, and then measuring cholesterol only in small dense LDL or sdLDL. This method is adaptable to high throughput automated analyzers, has been standardized, and is useful in the CVD risk assessment profile of the present invention.

Biomolecules, such as lipoproteins, separated via two-dimensional gel electrophoresis can be detected and identified with known immuno-detection techniques, such as immunoblotting: 1) for measuring specific protein component (i.e., Western blot analysis or Western blotting), 2) for measuring specific DNA component (i.e., Southern blot analysis or Southern blotting, and 3) for measuring specific RNA component (i.e., Northern blot analysis or Northern blotting). In Western blot analysis, proteins separated by electrophoresis in a polyacrylamide gel are transferred onto a membrane, followed by incubation with tagged first or tagged second antibodies. In Southern blot analysis, DNA fragments separated by electrophoresis on an agarose gel are transferred onto a membrane, incubated and hybridized with complementary (labeled) nucleic acid probes. In Northern blot analysis, RNA fragments separated by electrophoresis on an agarose gel are transferred onto one or more nitrocellulose membranes, incubated and detected with a suitable probe.

A typical Western blot analysis comprises the steps of preparing the protein samples, electrophoresis of the protein samples by one or two dimensional polyacrylamide gel, transferring the protein sample from the polyacrylamide gel to a membrane, blocking the membrane in a blocking solution (e.g., typically in PBS containing 3% BSA or 5% non-fat milk), followed by incubation of the membrane with tagged or plain monospecific first antibody diluted in PBS-Tween 20, and 3% BSA or 5% non-fat milk incubation mixture. After finishing incubation with the antibodies, unbound antibodies and tags are removed from the membrane by washing the membrane in the washing solution (PBS-Tween 20) several times until all residual nonspecific binding of tagged-antibody is removed. Often, plastic bags or open trays placed on a laboratory rocker or shaker are used to shake the incubation media during the incubation and washing cycles. Such processing means result in low efficiency and higher incidence of contamination of the immediate and larger environment. Further, these techniques present safety issues, due to the use of harmful toxins, including but not limited to use of mercury and/or radioactivity.

SUMMARY OF THE INVENTION

Methods and apparatus for preparing immunoblots for immuno-detection of biomolecules exist; however, they are tainted with low efficiency and contamination potential.

In view of the above, there is a need for a safe and effective method for producing immunoblots on membranes. Further, there is a need for apparatus to facilitate the safe and effective immunoblotting on membranes.

It is, therefore, an aspect of the present invention to provide a safe, efficient and cost-effective method and apparatus for immunoblotting on membranes.

It is another aspect of the present invention to provide an efficient and cost-effective method and apparatus for simultaneously casting multiple gels.

It is another aspect of the present invention to provide an improved method for separating, detecting and identifying biomolecules, including intact high density lipoprotein (HDL) particles.

It is another aspect of the present invention to provide for a method for the use of biomolecules separated, detected and identified via the improved method for separating, detecting and identifying biomolecules.

The present invention pertains to methods and apparatus for separating, detecting and identifying biomolecules, including, but not limited to, HDL particles. One present method involves the simultaneous casting of multiple gels, including the casting of a novel polyacrylamide gel. Another present method involves the separation of biomolecules using vertical agarose gel electrophoresis in the first dimension of a two-dimensional gel electrophoresis. Another present method involves the use of non-denaturing polyacrylamide gel electrophoresis for separating biomolecules, including lipoproteins, using the novel polyacrylamide gel in the second dimension. Another present method involves the use of the separated and immunoblotted biomolecules, such as HDL particles, resulting from methods of the present invention to assess CVD risk, evaluate the efficacy of lipid medications, and optimize patient therapy. One present apparatus facilitates the simultaneous casting of multiple gels. Another present apparatus facilitates the immuno-detection of separated biomolecules. This apparatus, comprising a special closed membrane incubation chamber and a rotator device for rotating the closed-chamber, is designed to improve the efficiency of immunoblotting on the membrane, as well as the disposal of harmful materials.

The methods and apparatus of the present invention provide greater efficiency, reduce exposure (toxin and/or oxidizing radiation) for workers, eliminate contamination issues, provide a means for safe and controlled handling and disposal of chemicals and any harmful materials, and reduce time and operational costs.

The above summary of the present invention is not intended to describe each illustrated embodiment or every implementation of the present invention. The figure and the detailed description that follow particularly exemplify these embodiments.

BRIEF DESCRIPTION OF THE DRAWINGS

The invention may be more completely understood in consideration of the following detailed description of various embodiments of the invention in connection with the accompanying images, in which.

Figure 1:
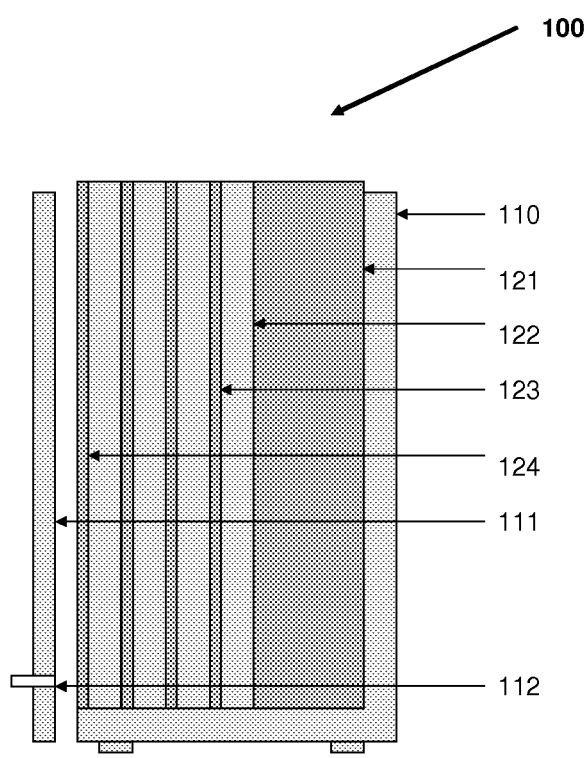
FIG. 1 is a cross-sectional illustration of the modified multiple-gel caster apparatus, according to an aspect of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention pertains generally to separation and immuno-detection of biomolecules. Specifically, the present invention pertains to methods and apparatus for separation of biomolecules via two-dimensional gel electrophoresis, methods and apparatus for immunoblotting any separated biomolecules that are transferred to supporting membrane, and method for the use of biomolecules processed via the methods and apparatus of the present invention, including their use in a clinical setting.

1. Definitions

The term "α-1 HDL particle" or "α-1", as used herein, refers to the apoA-I concentration in the HDL particles with a median size of about 11.0 nm. It is one of the most important HDL particles for predicting heart disease. This large particle delivers cholesterol to the liver. This HDL particle is large and lipid-rich; it contains 6 molecules of apoA-I, a large amount of free cholesterol and phospholipids (PL) on the surface, and cholesterol ester and TG in the core. This is the particle that interacts with scavenger receptor B1 (SRB1) in the liver and dumps cholesterol into the bile. A decreased level marks an inadequate HDL metabolism and is associated with increased risk for CVD. A value below 12.0 mg/dl is associated with increased heart disease risk in men and a value below 18.0 mg/dl is associated with increased heart disease risk in women, while a value between 12.0 mg/dl and 17.0 mg/dl in men, and between 18.0 mg/dl and 28.0 mg/dl in women is considered borderline. A value is above 17.0 mg/dl in men and above 28.0 mg/dl in women is considered normal.

The term "α-3 HDL particle" or "α-3", as used herein, refers to the apoA-I concentration in the HDL particles having a median size of about 8.00 nm. There is no established optimal or normal level for α-3; however, a ratio of α-1 to α-3 of less than 0.3 is an indication of abnormal HDL metabolism and increased risk of CVD.

The term "α-4 HDL particle" or "α-4", as used herein, refers to the apoA-I concentration in the HDL particles having a median size of about 7.42 nm. There is no established optimal or normal level for α-4; however, a ratio of α-1 to α-4 of less than 0.6 is an indication of abnormal HDL metabolism and increased risk of CVD.

The term "biomolecule", as used herein, refers to an organic molecule, particularly, a macromolecule (e.g., a protein or nucleic acid) in living organisms.

The term "HDL subfractionation", "two-dimensional gel electrophoresis of HDL particles", "HDL separation by two-dimensional gel electrophoresis", "two-dimensional gel electrophoresis" or "two-dimensional HDL separation", as used herein, refers to a technology that measures different HDL particles by directly separating the particles by size and charge, and then measuring the amount of the protein A-I in each particle. It assesses how well a person's HDL particles are functioning in order to help remove cholesterol from the body. This test not only measures the small HDL particles that pick up cholesterol from the artery wall but also the large HDL particles that deliver cholesterol to the liver. These small HDL and large HDL particles help provide very precise information about a person's heart disease risk. Also, measuring these particles helps to determine how well a therapy with medication(s) is working in a patient.

The term "high density lipoprotein cholesterol" or "HDL-C", as used herein, refers to the cholesterol measurement in plasma, after the removal of apoB-containing lipoproteins (VLDL and LDL particles). High levels of HDL cholesterol, above 60 mg/dl, protect against heart disease. A value between 40 mg/L and 60 mg/dl is considered borderline, while a low HDL cholesterol value, below 40 mg/dl in a man and below 50 mg/dl in a woman, is associated with an increased risk of heart disease.

The term "immunoblot", as used herein, refers to a blot in which a tagged ligand, such as an antibody, is used as the molecular probe. It also refers to a product resulting from a process by which separated biomolecules are allowed to adhere to any kind of supportive membrane sheets where they bind nonspecifically and then are subsequently identified by labeling with appropriately tagged antibodies.

The term "immuno-detection", as used herein, refers to separation and identification of a biological substance by means of binding an antibody to its antigen, and comprises the Western blotting, Southern blotting and Northern blotting techniques.

The term "membrane", as used herein, refers to a thin sheet of natural or synthetic material that is porous and possesses any kind of binding capacity (e.g., hydrophilic, hydrophobic, or has a capacity to bind to positively or negatively charged molecules) and retains biomolecules above a certain molecular size (usually ≥3 nm). Most commonly used membranes are produced from nitrocellulose, nylon, or polyvinylidene difluoride (PVDF).

The term "preβ-1 HDL particle", as used herein, refers to an important HDL particle for predicting heart disease. This HDL particle is quite small, contains 2 apoA-I and 16 phospholipid (PL) molecules. This is the particle that picks up cholesterol from the artery wall via the ABCA1 pathway.

An increased level marks an inadequate HDL metabolism and is associated with increased risk for CVD. A value above 20.0 mg/dl is associated with increased heart disease risk in both men and women, while a value between 15.0 mg/dl and 20.0 mg/dl in both men and women is considered borderline. A value below 15.0 mg/dl in both men and women is considered optimal.

It is to be understood that the singular forms of "a", "an", and "the", as used herein and in the appended claims, include plural reference unless the context clearly dictates otherwise.

2. Two-Dimensional Gel Electrophoresis and Immuno-Detection of Biomolecules

Immuno-detection of biomolecules is often performed with separated biomolecules, including biomolecules separated by two-dimensional gel electrophoresis. In one aspect of the present invention, similar to currently practiced techniques, the methods of the present invention involve the separation of biomolecules, for example, proteins (or lipoproteins), in a given sample, and the subsequent immuno-blotting of the separated biomolecule components using a ligand, particularly an antibody, monospecific to the biomolecules of interest. In one aspect of the invention, the biomolecules are separated by two-dimensional gel electrophoresis. The methods of the present invention are based on existing methods, however, the present invention provides improvements over existing methods and apparatus for facilitating the separation of biomolecules and the immuno-detection of any blottable parameters (e.g., protein, DNA, and RNA) on the membrane. These improvements, which are particularly effective for the separation and immunoblotting of HDL particles, include the semi-automation of the en mass (rather than individual) gel-pouring and immunoblotting steps which enable the analysis of an increased number of samples up to a hundred-fold. Regarding gel-pouring, the improvements include the introduction of vertical agarose electrophoresis (instead of the traditional horizontal or open top agarose electrophoresis), whereby agarose gel is casted into glass cassettes and electrophoresed while it is completely immersed in cold buffer; a novel type of a polyacrylamide gel (non-denaturing 3-35% concave gradient polyacrylamide gel); simultaneous multiple castings of this novel polyacrylamide gel; development of an inversely concentrated polymerization catalyst to facilitate the use of the wide range (3%-35%) of polymer (acrylamide) concentrations; and development of a multiple gel caster apparatus (as shown in FIG. 1). Regarding immunoblotting, the improvements include the development of an apparatus, comprising a closed incubation chamber and a rotating feature for rotating the closed-chamber, for safe and efficient immunoblotting of membranes (as shown in FIG. 2-FIG. 8).

The separation, via two-dimensional gel electrophoresis, of HDL particles having particle sizes in the range between 28 KD and 600 KD requires a special gel. The separation of whole HDL particles requires non-denaturing conditions, while this disclosed size range requires a density gradient gel. Hence, a novel 3-35% concave gradient polyacrylamide gel has been developed to address these requirements. This novel gel is produced by preparing two different concentrations of gel stock—a lighter gel and a heavier gel. The lighter gel stock contains 3% acrylamide by weight, and the heavier gel stock contains 58% acrylamide by weight. The heavier gel stock contains about 50% less catalyst (TEMED and ammonium persulfate) for gel polymerization. Gel stocks are placed into a gradient former, sized for this purpose. The lighter gel stock (twice as much as the heavier gel stock) is put in the larger chamber which has twice the volume of the chamber receiving the heavier gel stock. There is a closable valve between the two chambers to facilitate the movement of the heavier gel stock into the chamber of the lighter gel stock at the rate of the lighter gel being pumped into the casting apparatus. The lighter gel chamber contains a stirrer to mix the incoming lighter gel with the gel in the chamber. This setting produces a concave concentration gradient gel, which has been optimized for HDL particle separation; however, other concave concentration gradient gels can be optimized for separation of other types of biomolecules based on this process. The gradient of polymerization catalyst ensures that the gels start polymerizing at the bottom a bit faster than at the top, but without reducing the polymerization at the top dramatically, which would make the gels unusable. In addition, the introduction of the polymerization gradient prevents excess heat production, which is a side effect of acrylamide polymerization and which would cause heat convention in the gel, thereby destroying the concentration gradient. The gels are poured into a gel caster apparatus, inside of a cold (about 4° C.) cabinet, in order to avoid premature polymerization, and then the gels (including the casting apparatus containing the gels), are placed into another cabinet, set at a temperature in the range of about 15° C. to 16° C., for polymerization.

Although non-denaturing polyacrylamide gel electrophoresis for separating lipoproteins is a technique known in the art [see e.g., Asztalos, B. F., Sloop, C. H., Wong, L., Roheim, P. S.; "Two-dimensional electrophoresis of plasma lipoproteins: recognition of new apo A-I-containing subpopulations", *Biochim Biophys Acta.*, 1993 Sep. 8; 1169(3):291-300], pouring this type of gels en mass is not readily available in the art and has been a major difficulty to overcome. However, the present invention overcomes this difficulty by utilizing a novel gel-casting technology for casting multiple gels, preferably from four to fifty gels, simultaneously. Preferably, this multiple-gel casting technology is used for the casting of the 3-35% non-denaturing concave gradient polyacrylamide gel of the present invention. This aspect of the present invention can be utilized for the simultaneous multiple casting of any gel that can benefit from simultaneous multiple casting.

This novel gel-casting technology involves the use of a multiple gel casting apparatus. The multiple gel casting apparatus is constructed by modifying a commercially available multiple gel caster (e.g., Hoefer® SE 615 caster, available from Hoefer, Inc., Holliston, Mass.), as shown in FIG. 1, although a such apparatus can be constructed from the components and procedure disclosed herein without modifying an existing multiple gel caster. The multiple gel caster apparatus 100 of the present invention comprises a multiple gel caster frame 110 (hereinafter, "gel caster"), a lid 111, which may comprise a seal therein to facilitate the secure closure of the gel caster 110 therewith, and a slotted spacer 124, for placement in front of the gel caster 110, all of which are fabricated from any material suitable for their purpose, preferably, an acrylic material. The gel caster 110 is modified by shortening the depth of the commercially available gel caster with the use of a space block 121 to accept a plurality of gradient gel cassettes 122. The space block 121 is fabricated from any material suitable for its purpose, preferably, an acrylic material. This modification is made to provide better equalization of the gradient across the multiple gels that are to be poured simultaneously. The aspect of the present invention shown in FIG. 1 comprises a gel caster 110 modified to accept four gel cassettes 122. The gel caster 110 is also modified to comprise a heat dissipating means 123 placed between the gel cassettes 122.

Heat dissipating means 123 may be any suitable material to block excess heat convention between gel cassettes 122 during the polymerization, preferably, one or more acrylic sheets, each having a thickness to suit its purpose, preferably, a thickness of about 3 millimeters ["mm"] (0.12 inch) ["in."]; the other two dimensions of the heat dissipating means 123 are fixed by the corresponding dimensions of the gel caster 110. The gel cassette 122 preferably comprises glass plates to facilitate the uniform casting of the gels therein.

This novel gel-casting technology also involves the application of an inversely concentrated polymerization catalyst (rather than the widely used flat concentration polymerization catalyst) to allow the gels to polymerize slowly, starting at the bottom of the gel caster 110 and moving upward gradually. The inversely concentrated polymerization catalyst (TEMED and ammonium persulfate; the concentration of each component varies depending on the type and concentration of gels used, the time/speed of pouring, and the temperature of the environment) was developed to facilitate the use of the wide range (3%-35%) of polymer (acrylamide) concentrations used herein.

The multiple gel castings are produced utilizing the multiple gel caster apparatus of the present invention, whereby gels are poured into the gel caster 110 via the port 112, located at the bottom of the gel caster 110, inside of a cabinet where the gels are maintained at a temperature of about 4° C., and then the gels are placed into another cabinet, set at a temperature of about 15.5° C., until the gels polymerize to yield gel castings having a thickness of about 3 mm (0.12 inch) each. These conditions allow the gels to polymerize from the bottom to the top gradually, without producing excess amount of heat, as an excess amount of heat would cause heat convention in the gel cassettes 122, which would ruin the gel concentration gradient.

The improvements to the electrophoresis gels result in various benefits, which include the following benefits. Regarding the "vertical agarose" gel: resolution is improved among the different sized biomolecules; the transferability of the agarose strips to the polyacrylamide gel is improved, due to the uniform size of the gel resulting from being cast in the gel cassette; and, production is facilitated as this type of casted agarose gel can be prepared ahead of time and stored for several days before use (similar to the polyacrylamide gel), unlike the traditional "horizontal" (open top) type agarose gel (which has to be prepared shortly before use) used widely prior to the casted-gel technology of the present invention. Regarding the novel concave gradient polyacrylamide gel: resolution is improved among the different sized biomolecules (e.g., HDL subclasses); and, gel pouring efficiency is improved due the capability of simultaneous multiple castings.

Casted gels are used in the separation of biomolecules via two-dimensional gel electrophoresis. In one aspect of the present invention, two-dimensional gel electrophoresis is used for resolving multiple native nuclease activities in a protein. This involves separating the proteins by gel electrophoresis in the first dimension under non-denaturing conditions according to isoelectric point; then separating those separated proteins by gel electrophoresis in the second dimension under non-denaturing conditions according to size and mass-to-charge ratio under conditions which inhibit nuclease activity, and with a polynucleotide nuclease substrate being incorporated into the second-dimension gel; then incubating the second-dimension gel under nuclease-activating conditions; and visualizing nuclease activities in the gel. In one aspect of this method, the slab gel electrophoresis is at approximately 12.5 mA per gel. In one aspect of this method, the incubation of the slab gel after electrophoresis is in a citrate-phosphate buffer, using a volume of about 50 ml/gel. In one aspect of this method, the nuclease is DNAase. In one aspect of this method, the nuclease is RNAase. In one aspect of this method, the gel is incubated in the presence of manganese and calcium cations. In one aspect of this method, a sample of serum or plasma is used for providing the protein for separation. In one aspect of this method, the sample for providing the protein for separation comprises solubilized intracellular proteins. In one aspect of this method, the Tris-HCl is employed as non-denaturing solubilizer for the proteins in the sample.

In one aspect of the present invention, the gels casted via the multiple gel casting apparatus of the present invention are utilized in the two-dimensional electrophoresis separation of biomolecules. In one aspect, the gels casted via the multiple gel caster are the agarose gel (employing the "vertical agarose" technique disclosed hereinabove), used in the first dimension of the electrophoresis, and the polyacrylamide gel (the novel non-denaturing 3-35% concave gradient polyacrylamide gel disclosed hereinabove), used in the second dimension of the electrophoresis. In one aspect of the present invention, the biomolecules are HDL particles separated by two-dimensional gel electrophoresis, and the separated HDL particles are transferred (via standard electro-transfer method) to an immunoblotting membrane, preferably, a stack of immunoblotting membrane sheets, for immuno-detection. The immunoblotting membranes for use herein are processed via the novel apparatus also disclosed in the present invention [see Section 3, hereinbelow]. The membranes are incubated with selected ligands, preferably antibodies, in the closed-chamber of the rotating closed-chamber membrane incubation apparatus of the present invention. The antibodies useful herein include any antibody that is monospecific to the biomolecules of interest, for example: for immunoblotting of HDL particles, antibodies would be monospecific to the lipoproteins of interest. The antibodies for use herein may be labeled (i.e., tagged), or otherwise detectable via any suitable technique. During the incubation cycle, the separated biomolecules, such as separated HDL particles, bind to the membranes, whereby the significant portion of the particles is captured on the membranes. The special rotating component of the present apparatus improves the uniform mixing of antibodies in the incubation media, which increases the chance of the antibody binding to its antigene, and thus improves the efficiency of the immunoblotting. The uniform mixing is further enhanced via the use of a horizontal mixing means. This binding results in the formation of discrete and uniquely positioned spot patterns on the membranes, and thereby facilitating a more accurate detection and identification of the separated particles. The tagged antibody bound specifically to the biomolecule of interest, such as a protein, is then visualized with any suitable visualization technique, preferably an image analyzer.

Any incubation media suitable for use with and in accordance to existing immunoblotting techniques may be used in the present immunoblotting method; however, the incubation media PBST (phosphate buffer saline with detergent TWEEN 20) containing 5% dry milk and the specific antibodies for a given sample is the preferred incubation media for use herein, particularly with employment of the Western blotting technique.

Any washing solution suitable for use with and in accordance to existing immunoblotting techniques may be used in the present immunoblotting method; however, the washing solution PBST is the preferred washing solution for use herein, particularly with employment of the Western blotting technique.

Although the present methods for two-dimensional gel electrophoresis and immunoblotting is discussed in greater detail with respect to HDL particles, these methods are suitable for use with any gel based electrophoretic separation, and for any immunoblotting technique for the immunodetection of separated biomolecules, such as the Western blot (for protein analysis), Southern blot (for DNA analysis), or Northern blot (for RNA analysis) techniques.

3. Rotating Closed-Chamber Membrane Incubation Apparatus

Figure 2:
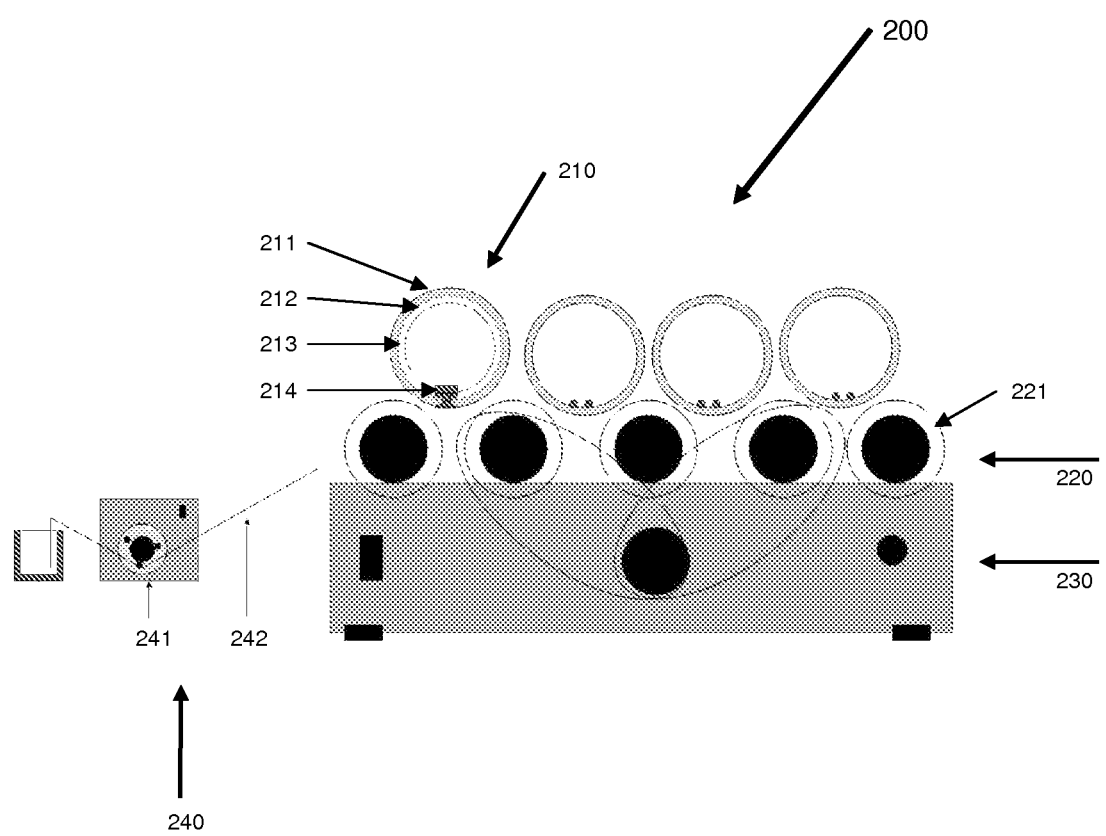
FIG. 2 is an illustration of a rotating closed-chamber membrane incubation apparatus for small to mid-scale processing of immunoblots, according to an aspect of the present invention.
Figure 4:
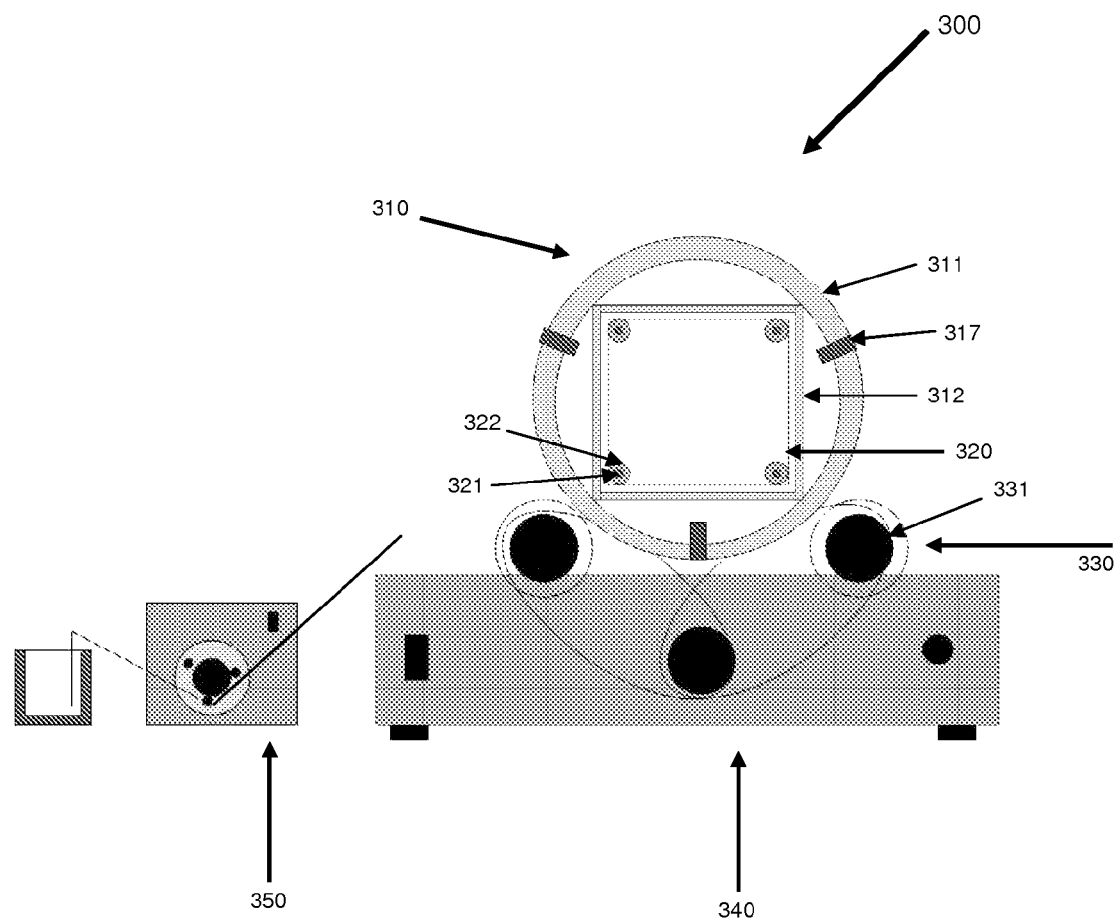
FIG. 4 is an illustration of a rotating closed-chamber membrane incubation apparatus for large-scale processing of immunoblots, according to an aspect of the present invention.

Existing technologies for producing immunoblotting membranes raise certain issues, including the use of open containers and sealed plastic bags, which are not suitable for the use of harmful materials, such as any toxic or oxidizing radioactivity necessary for the preservation and quantitative analyses of any biomolecules. Hence, a rotating closed-chamber membrane incubation apparatus, disclosed herein, has been developed to enable the safe use of necessary harmful materials without the threat of toxic and radioactive contamination, among other advantages over existing technologies. The present apparatus for immunoblotting involves at least one rotatable or rollable, openable (but preferably hermetically sealed during the procedure) closed-chamber, having any dimension in any of the x-, y- and z-axis, for incubation of blotting membranes, and a rotator component, which may be any device that can provide suitable rotation, preferably uniform rotation, to the closed incubation chamber, preferably, the rotation of the closed-chamber is perpendicular to the plane of the membranes placed in the closed-chamber, more preferably, the rotator component is a roller-based device (hereinafter "roller/rotating"), as shown in FIG. 2 and FIG. 4. The present apparatus may comprise any number of closed-chambers, such as one or four chambers, as shown in FIG. 4 and FIG. 2, respectively. The closed-chamber may comprise any size, shape or configuration. The closed-chamber may be a single-chamber or a dual-chamber type; the dual-chamber comprises an outer component and an inner component. The outer component can be in the shape of a cylinder if it is used on a roller, as shown in FIG. 2, or can be any shape if it is used with other types of rotators. The inner component can be shaped and sized to accommodate the shape and size of the membranes being used, such as a square, a triangle, or an octagon, in the x- and y-axis, with a number of sides in the z-axis that correlates to the shape in the x- and y-axis. In one aspect of the present invention, the apparatus comprises one closed single-chamber. In one aspect, the apparatus comprises multiple closed single-chambers, as shown in FIG. 2. In one aspect of the present invention, the apparatus comprises one closed dual-chamber, as shown in FIG. 4. In one aspect, the apparatus comprises multiple closed dual-chambers. In one aspect of the present invention, the closed single- or dual-chamber(s) is rotated via a rotator. In one aspect, the closed-chamber(s) is placed on a roller type rotator connected to a driving means, for rotation thereof; in another aspect, the closed-chamber(s) is directly connected to the driving means, for rotation thereof. The driving means may be any device that can facilitate the rotation of the closed-chamber(s), preferably, a motor. The closed-chamber is preferably hermetically sealed to prevent the incubation media from spilling to the outside of the chamber. In the dual-chamber systems, the inner component of the chamber is fixed, preferably permanently fixed, inside of the outer component of the chamber and closed off from the dead space between the two components of the chamber. The hermetic sealing secures the incubation media inside of the inner component of the dual-chamber. The dual-chamber system is practical when at least 10 membranes are processed. The length of the incubation chamber can be sized to accommodate any number of membranes, but the vertical mixing may limit its practical use involving a great quantity of membranes.

Figure 3:
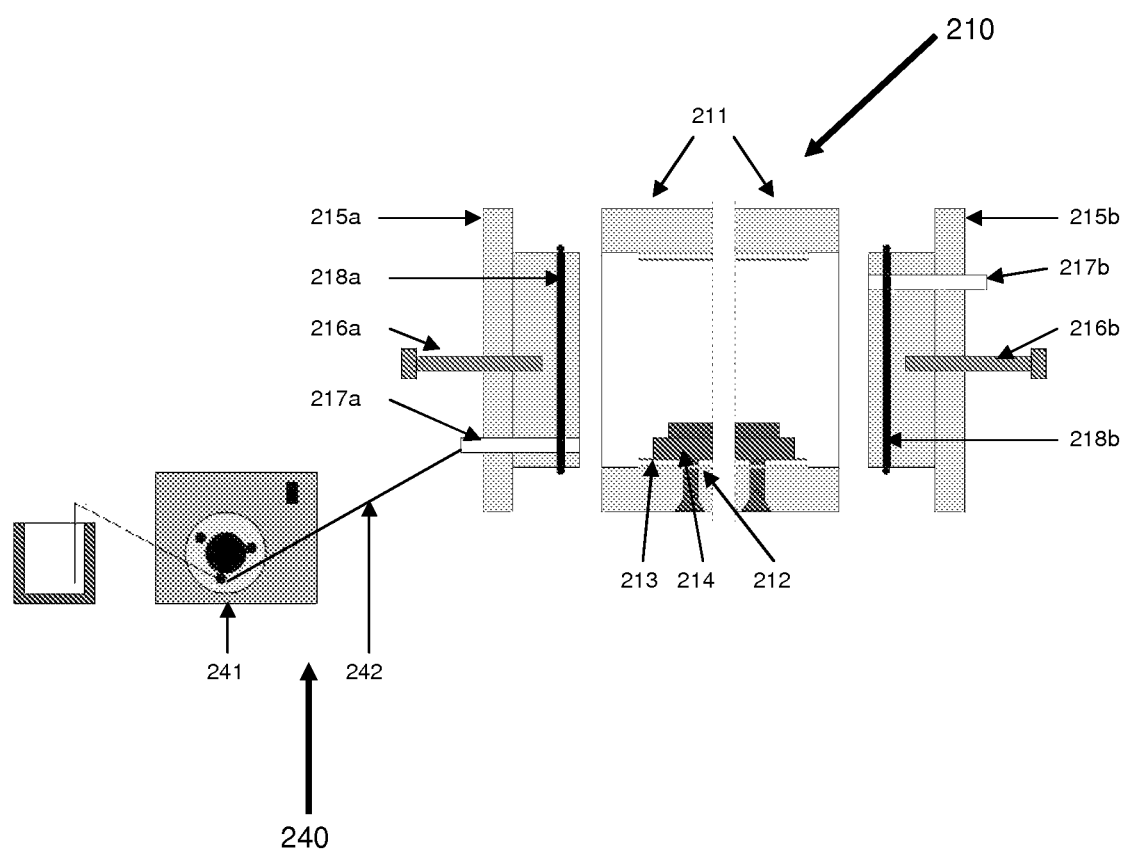
FIG. 3 is an illustration of a cross-sectional view of the sealed incubation chamber connected to the micro pump component, of the rotating closed-chamber membrane incubation apparatus shown in FIG. 2, according to an aspect of the present invention.

In one aspect of the present apparatus, shown in FIG. 2 and FIG. 3, the rotating closed single-chamber membrane incubation apparatus 200 comprises four closed-chamber membrane incubation components 210, a roller/rotating component 220, a housing component 230, and a pump component 240. In such configuration of the present apparatus, the closed membrane incubation chamber is utilized to process small or medium-sized batches of membranes, preferably up to 20 membranes, simultaneously, as shown in FIG. 2.

Each closed-chamber membrane incubation component 210 comprises a cylindrical body 211 having an interior and an exterior surface and two open opposing ends. Each cylindrical body 211 is fabricated from a material suitable for its purpose, preferably, a polycarbonate material. The size of the closed-chamber is designed to accommodate the size and number of membranes in use. Each membrane incubation chamber component 210 comprises two covers 215a and 215b, preferably plugs, configured to fit each of the two open opposing ends of the cylindrical body 211, in order to securely close each end of the cylindrical body 211. At least a portion of one or both of the covers 215a and 215b may be temporarily or permanently attached to cylindrical tube 211. The plugs 215a and 215b are removed partially or completely from the cylindrical body 211 to facilitate the insertion or removal of the membranes 213 therefrom. Preferably, each membrane incubation chamber component 210 comprises two O'rings 218a and 218b, one placed between one end of the cylindrical body 211 and plug 215a and another placed between the other end of the cylindrical body 211 and plug 215b, as shown in FIG. 3, to facilitate the sealing, preferably hermetic sealing, of both ends of the closed chamber membrane incubation component 210. The plugs 215a and 215b are fabricated from a material suitable for their use, preferably, a polycarbonate material. Each of the two plugs 215a and 215b comprises valve, preferably a quick release shut-off valve, 217a and 217b, respectively. The valves 217a and 217b are fabricated from any material suitable for their use, preferably, non-corrosive material. One of the two valves 217a/217b is used as a fluid valve, for input/output of the incubation media and the washing solution, and the other valve is used as an air valve; the two valves can be used interchangeably for the stated purposes. The shut-off valves 217a and 217b also serve to facilitate the safe use and disposal of any harmful materials that may be utilized in the immunoblotting process. The membrane incubation component 210 is designed to contain the incubation media; preferably, incubation media is placed into the membrane incubation component 210 in a quantity sufficient to cover the membranes in the chamber (preferably, 150-200 ml incubation media per five membranes). The rotating closed-chamber membrane incubation apparatus 200 may also comprise a means 216 for holding the closed-chamber membrane incubation components 210 in place on the roller/rotating component 220, e.g., a bumper.

The closed-chamber membrane incubation component 210 shown in FIG. 3 comprises a membrane holding means 212 for holding the membranes 213 in position against the interior surface of the cylindrical body 211. The membrane holding means 212 is fabricated from any material suitable for its use, and preferably it is a screen or mesh-type material. The membrane holding means 212 is secured to the interior surface of the cylindrical body 211 and held in position with at least one, preferably two, rods 214, and a fastening means comprising a screw and/or bolt. The rods 214 and the fastening means are fabricated from any material suitable for their use, preferably, a metal suitable for use in salty conditions, more preferably, brass. The quantity and placement of rods 21, as described are suitable for membranes having a certain shapes; the quantity and placement of the rods may differ to accommodate membranes having other configurations. Each rod 214 comprises dimensions suitable for its purpose, preferably a diameter of about 3.2 mm (0.125 in.) and a length equivalent to the length of the cylindrical body 211.

The roller/rotating component 220 is utilized for rolling the cylindrical body 211 to increase incubation effectiveness of the membranes 213. The roller/rotating component 220 comprises any quantity of rolls 221 to facilitate the rotation of a given quantity of closed membrane incubation components 210 (e.g., the embodiment illustrated in FIG. 2 contains five rolls 221 to facilitate the rotation of four closed membrane incubation components 210), and the electronic and mechanical components necessary for the proper functioning thereof. Each roll 221 is fabricated from any material suited for its purpose, preferably, rubber, and comprises a metal ball bearing axle to facilitate the rolling action of the roll 221. Any suitable commercially available bottle roller may be altered, such as making it larger and adding ball bearings thereto, for use as the roller/rotating component 220. The above-mentioned setting of the membranes 213 in the cylindrical body 211 allows for the membranes to rotate in parallel with the axle of the roll 221, which enables the significant reduction of incubation media used per membrane.

The housing component 230 is utilized as a stand for the roller/rotating component 220 and the closed-chamber membrane incubation components 210, as well as to house the driving means for facilitating the rotation of the closed membrane incubation component 210, as a motor, the potential meter, the on/off switch, and the electronics board comprising transistor(s), resistor(s), etc., of the apparatus 200. The motor suitable for use herein may be any motor capable of running 5 revolutions per minute (rpm) to 200 rpm at about 0.4 horsepower.

The pump component 240 is utilized to pump the incubation media, as well as the washing solution, in and out of the closed-chamber membrane incubation component 210. The pump component 240 comprises a pump 241, preferably a peristaltic micro pump, and a fluid transfer means 242, preferably, a tubing. The micro pump 241 suitable for use herein may be any pump capable of delivering 200 milliliter (ml) to 4000 ml of volume per minute, preferably, a peristaltic MasterFlex® pump having such a capability (available from Cole-Parmer Instrument Company, Vernon Hills, Ill.). The tubing 242, comprising two opposing ends and capable of engagement with the valve 217a or 217b, is utilized for the transfer of any of the fluids used in the process, e.g., the incubation media and the washing solution, into or out of the closed incubation chamber. The tubing 242 is selected for proper fit with the pump 241 being used (e.g., sized for the pump head type and speed) and to provide proper flow of fluids therethrough. The micro pump 241 assists in the delivery of the incubation media, as well as the washing solution, to, or their removal from, the closed chamber membrane incubation component 210 via the tubing 242 and the valve 217a or 217b.

The incubation apparatus 200 is designed to decrease the need for use and disposal of harmful chemicals, to improve membrane incubation efficiency, and to decrease operational cost and time. This aspect of the present apparatus, shown in FIG. 2 and FIG. 3, allows simultaneous processing of up to 20 membranes 213 (five membranes 213 per closed-chamber membrane incubation component 210, and up to four closed membrane incubation chamber components 210 per roller/rotating component 220), yielding about 2,000-3,000 blots per setting per year. As such, it is economical for analyses of small and medium-sized batches of membranes.

The Western blot technique in use with gel electrophoretic separation is widespread; however, working with a large number of large-sized membranes is not trivial. The configuration of the rotating closed-chamber membrane incubation apparatus of the present invention, shown in FIG. 4, overcomes this issue by facilitating the processing of a large quantity of membranes, preferably up to 100 membranes, of any size simultaneously, and thereby decreasing the need for manpower, space time, money, while minimizing contamination of incubation media and spillage of contaminated incubation media in the laboratory environment. Moreover, the closed incubation chamber allows the user to securely handle and dispose the incubation media, preferably via an attached peristaltic pump, if the media contains any harmful material. In one aspect of the present apparatus, shown in FIG. 4, FIG. 7 and FIG. 8, the rotating closed dual-chamber membrane incubation apparatus 300, comprises a closed membrane incubation component 310, a removable membrane holder component 320, a roller/rotating component 330, a housing component 340, and a pump component 350.

Figure 5A:
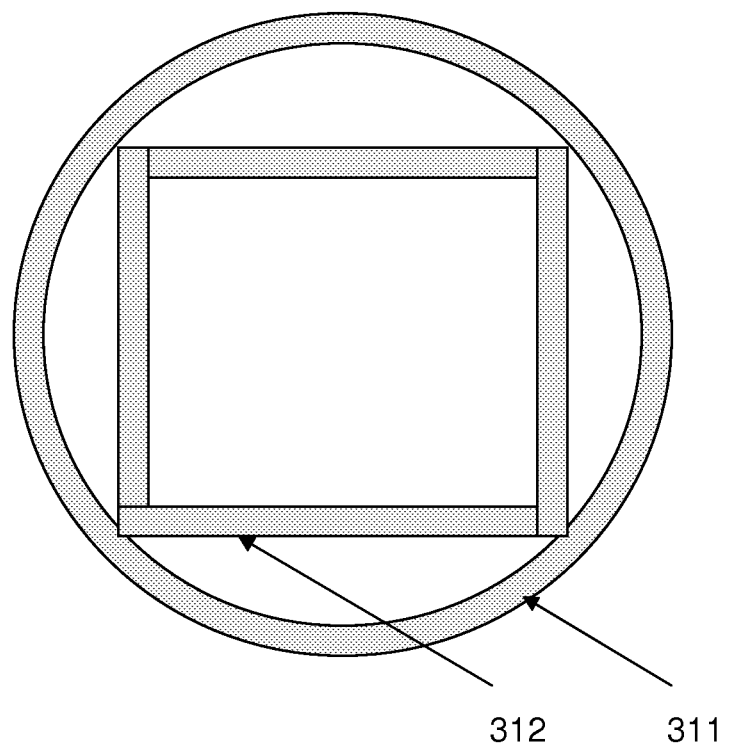
FIG. 5a is an illustration of a cross-sectional view of the outer component containing the inner component of the closed incubation chamber, of the rotating closed-chamber membrane incubation apparatus shown in FIG. 4, according to an aspect of the present invention.
Figure 5B:
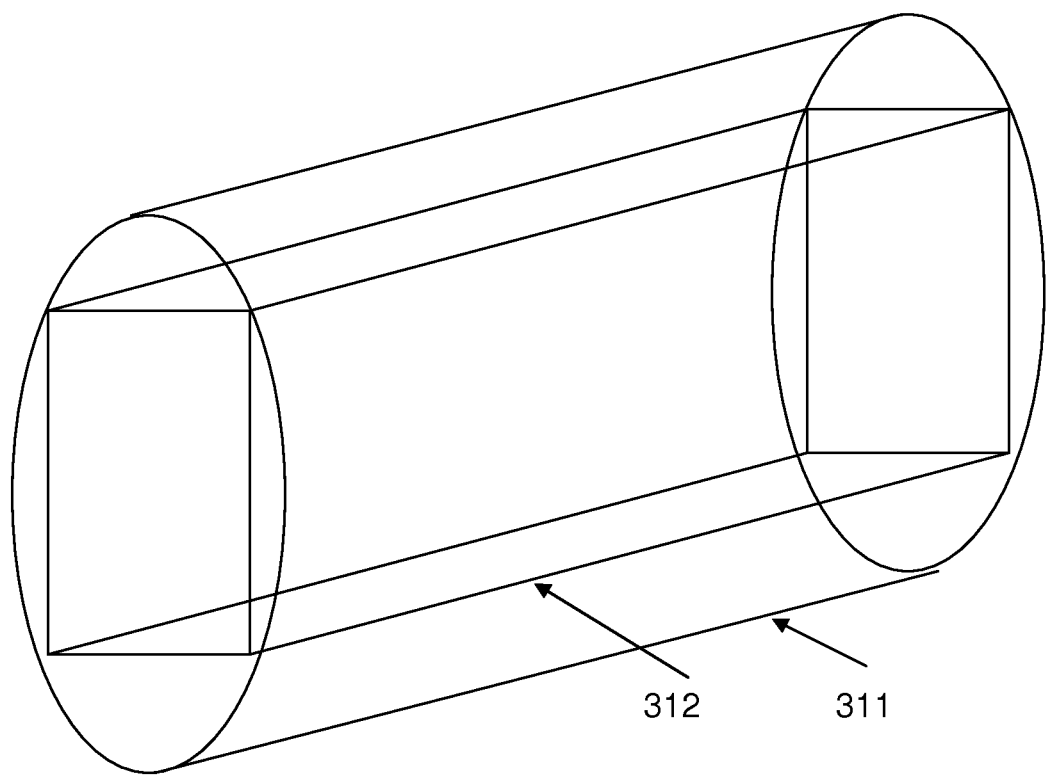
FIG. 5b is a 3-dimensional illustration of a side view of the outer component containing the inner component of the closed incubation chamber, of the rotating closed-chamber membrane incubation apparatus shown in FIG. 4, according to an aspect of the present invention.
Figure 7:
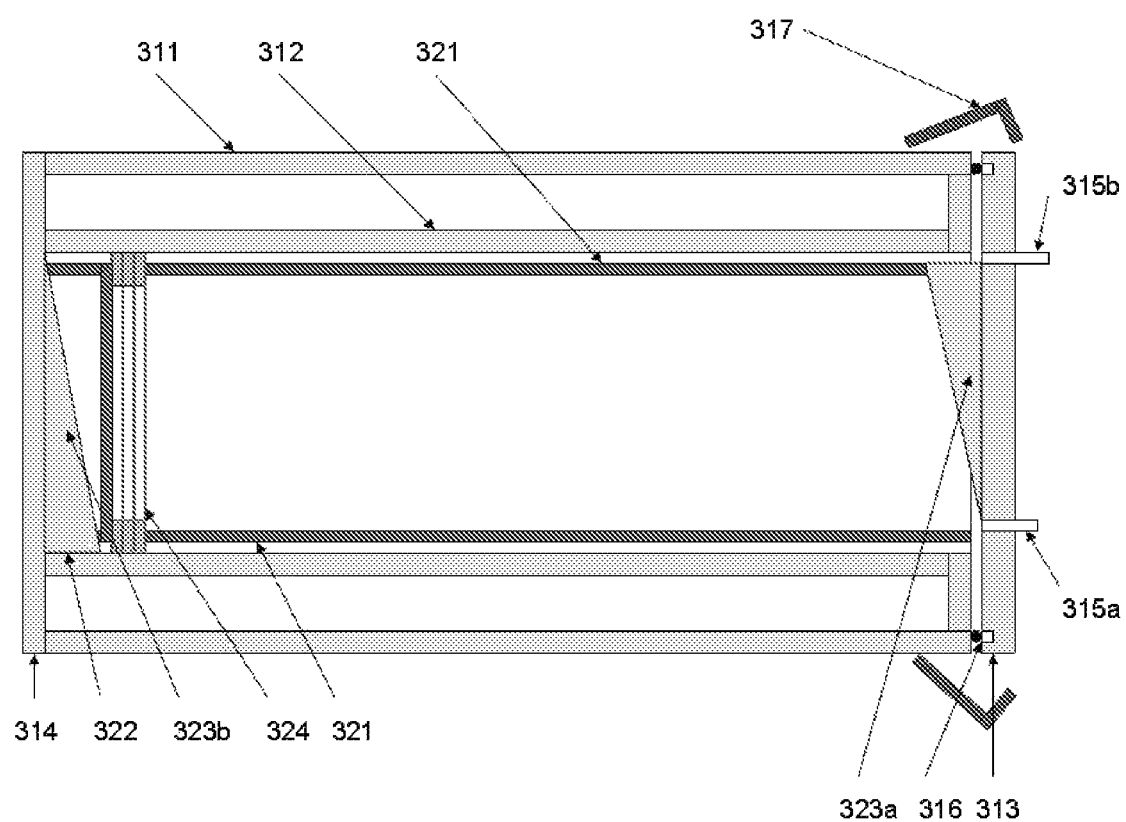
FIG. 7 is an illustration of a cross-sectional view of the sealed and clamped closed incubation chamber containing the membrane holder, of the rotating closed-chamber membrane incubation apparatus shown in FIG. 4, according to an aspect of the present invention.

In one aspect of the present apparatus, the closed membrane incubation component 310 comprises an outer component 311 in the shape of a cylindrical tube comprising a tubular body (hereinafter "cylindrical tube 311"), having an interior and an exterior surface and two open opposing ends, an inner component 312 of any shape, preferably, a square in the x- and y-axis (hereinafter "square incubation chamber 312"), having an interior and an exterior surface and two open opposing ends, and configured for placement inside of the cylindrical tube 311, two covers 313 (referred to as the lid) and 314 (referred to as the bottom cover) configured to fit each of the two open opposing ends of the cylindrical tube 311, and two valves, preferably quick release shut-off valves, 315a and 315b, as shown in FIG. 5a, FIG. 5b and FIG. 7. The cylindrical tube 311, the covers 313 and 314, and the square membrane incubation chamber 312 are fabricated from any material suitable for their purpose, preferably, a polycarbonate material. In one aspect, one or both of the covers 313 and 314 are detached from the cylindrical tube 311. In one aspect, at least a portion of one or both of the covers 313 and 314 are temporarily or permanently attached to at least a portion of the cylindrical tube 311. The covers 313 and 314 are used for closing the cylindrical tube 311; however, one of both of the covers 313 and 314 are removed partially or completely from the cylindrical body 311 to facilitate the insertion or removal of the membrane holder 320 from the incubation chamber. The cylindrical tube 311 and the square incubation chamber 312 can have any dimension; preferably, the cylindrical tube 311 has an inner diameter suitable for the size of membrane(s) in use, preferably not more than about 6.4 mm (0.25 in.) larger than the dimension (e.g., diameter) of the membrane to minimize the use of incubation media. One of the two valves 315a/315b is used as a fluids valve, for input/output of the incubation media and the washing solution, and the other valve is used as an air valve; the two valves can be used interchangeably for the stated purposes. The shut-off valves 315a/315b also help to facilitate the safe use and disposal of any harmful materials that may be utilized in the immunoblotting process. The square incubation chamber 312 is placed inside of the cylindrical tube 311 in such a manner to permit the communication of at least a portion of the exterior surface, preferably the four corners, of the square membrane incubation chamber 312 with at least a portion of the interior surface of the cylindrical tube 311. The square membrane incubation chamber 312 is fixed, temporarily or permanently, via any suitable affixing means, to the interior surface of the cylindrical tube 311. The square incubation chamber 312 is designed to contain the incubation media; preferably, incubation media is placed into the square incubation chamber 312 in a quantity sufficient to occupy about 75% of its volume. The membranes 324 are assembled and secured into a removable membrane holder 320 outside of the incubation chamber and then positioned in place inside of the square incubation chamber 312.

Figure 6:
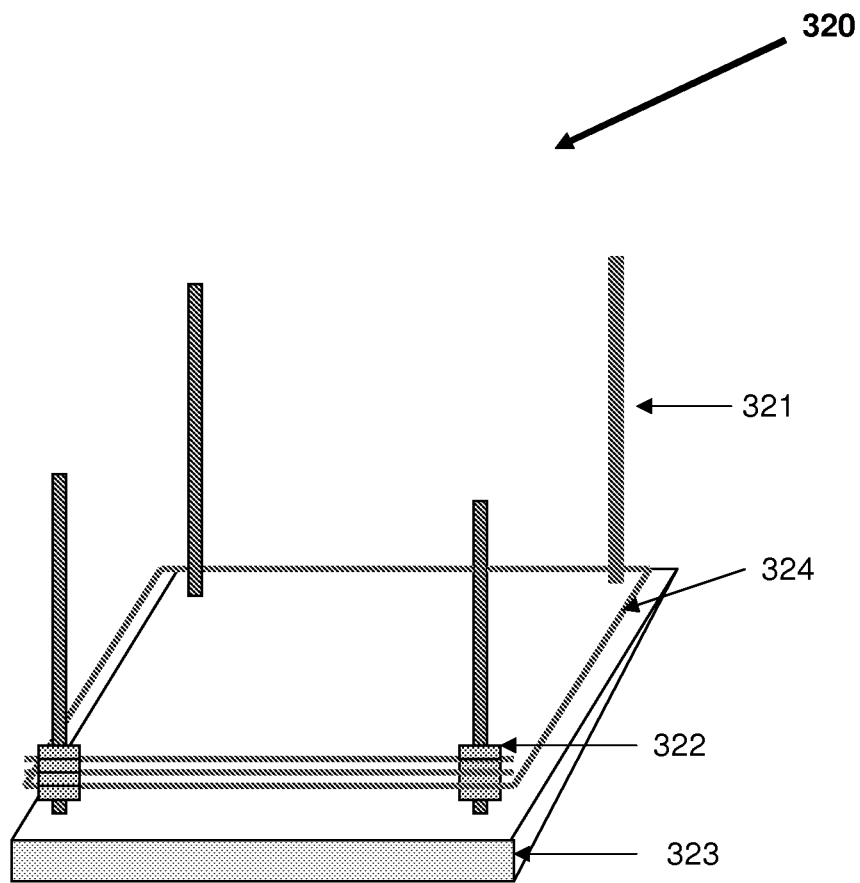
FIG. 6 is a 3-dimensional illustration of the membrane holder, of the rotating closed-chamber membrane incubation apparatus shown in FIG. 4, according to an aspect of the present invention.
Figure 8:
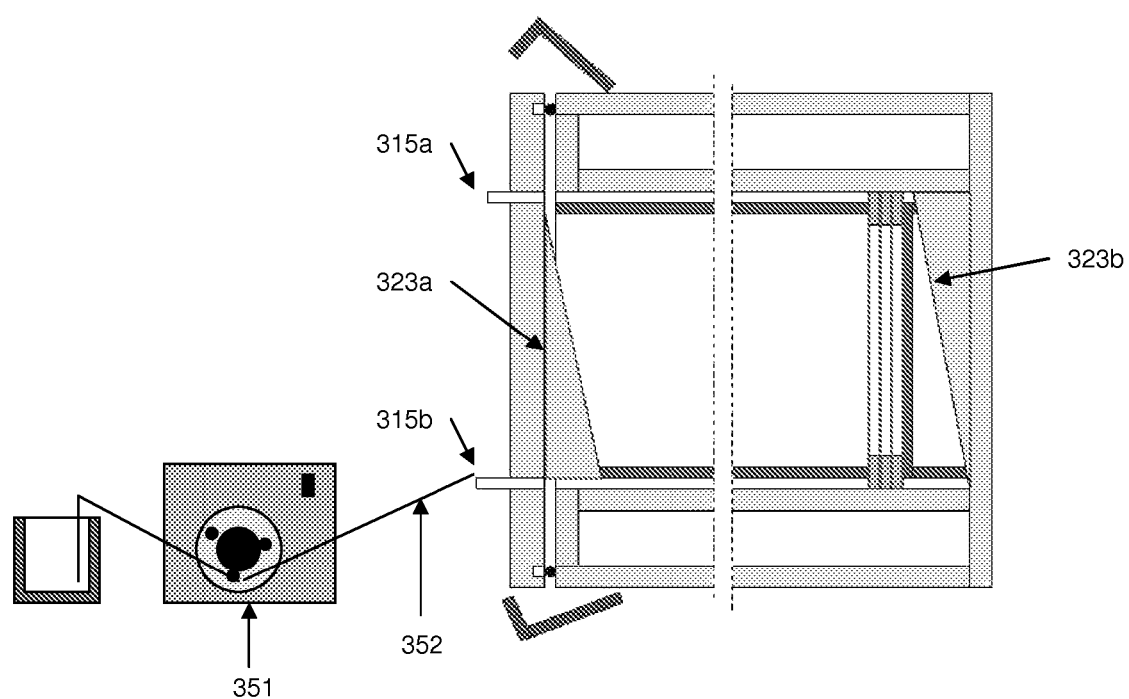
FIG. 8 is an illustration of a cross-sectional view of the sealed and clamped closed incubation chamber connected to a micro pump, of the rotating closed-chamber membrane incubation apparatus shown in FIG. 4, according to an aspect of the present invention.

The removable membrane holder component 320 is designed to hold the membranes 324 in place inside of the square incubation chamber 312 during the incubation of the membranes 324, as shown in FIG. 8. Membrane holder component 320, which can accommodate any quantity of membranes 324, preferably up to 100 membranes, makes the processing of a large-sized batch of membranes economical and yielding up to 25,000 blots per chamber 310 per year. The removable membrane holder component 320 comprises a quantity of rods 321, preferably four rods, to hold the membranes 324 in a stack arrangement (as illustrated in FIG. 6), a quantity of separation means 322 (hereinafter "spacers"), preferably four spacers per each membrane 324 (each spacer being disposed preferably near the perimeter of a membrane, more preferably, at the corner of each membrane) to separate one membrane from another membrane in the stack of membranes 324 placed in the membrane holder component 320. The quantity and placement of the rods 321 and spacers 322 as described are suitable for membranes having a certain polygonal shape in the x- and y-axis, such as a square or a rectangle; the quantity and placement of the rods and spacers will differ to suit membranes having other configurations, and thus a membrane holder component 320 comprising membranes of different configuration shall comprise at least one rod 321, and at least one spacer 322 per membrane 324. The removable membrane holder component 320 also comprises two blocks 323a and 323b, which serve as the mixing means to facilitate the horizontal mixing of the incubation media. The rods 321 and spacers 322 are fabricated from the same material suitable for their use, preferably, a metal suitable for use in salty conditions, more preferably, brass. Each rod 321 comprises dimensions suitable for its purpose, preferably a diameter of about 3.2 mm (0.125 in.) and a length enabling its fit into the square incubation chamber 312. Each spacer 322 comprises dimensions suitable for its purpose, preferably a thickness of about 3.2 mm (0.125 in.) and a diameter of about 6.4 mm (0.25 in.). The mixing means 323 are fabricated from any material suitable for their purpose, preferably, an acrylic material, and, preferably, constructed to have minimum volume at one end and maximum volume at the other end (as shown in FIG. 6). Preferably, each of the two mixing blocks 323a and 323b are placed into the membrane holder component 320 such that they form the two opposite ends thereof, as shown in FIG. 7. Preferably, the membrane holder component 320 is placed into the square incubation chamber 312 such that each of the two mixing blocks 323a and 323b are at each of the two ends of the square incubation chamber 312, as shown in FIG. 7 and FIG. 8.

It is important to maintain the membranes 324 in a closed environment in the square incubation chamber 312; thus, the incubation chamber is sealed, preferably hermetically sealed. To facilitate the hermetic sealing, an O'ring 316 is placed between one end of the cylindrical body 311 and lid 313, as shown in FIG. 7; alternatively, the lid 313 may be constructed to comprise the O'ring 316. A suitable quantity, e.g., at least one, preferably three, of clamping means 317, preferably clamps, are used to maintain the hermetic seal. The clamping means 317, fabricated from any material suitable for their purpose, preferably stainless steel, are selected to provide a secure fit over the closed membrane incubation component 310. As such, the closed membrane incubation component 310 is designed to improve the membrane incubation efficiency.

The roller/rotating component 330 is utilized for rolling the closed membrane incubation component 310 to increase incubation effectiveness of the membranes 324. The roller/rotating component 330 comprises any quantity of rolls 331 to facilitate the rotation of a given quantity of closed membrane incubation components 310 (e.g., the embodiment illustrated in FIG. 4 contains two rolls 331 to facilitate the rotation of one closed membrane incubation component 310), and the electronic and mechanical components necessary for the proper functioning thereof. Each roll 331 is fabricated from any material suited for its purpose, preferably, rubber, and comprises a metal axle equipped with ball bearing(s) to facilitate the rolling action of the roll 331. Any suitable commercially available bottle roller may be altered, such as making it larger and adding ball bearings thereto, for use as the roller/rotating component 330. The sealed membrane incubation component 310, comprising the square membrane incubation chamber 312 comprising the membrane holder component 320 comprising membranes 324, is placed on the roller/rotating component 330 such that the membrane sheets 324 are positioned perpendicular to the rotation axis.

The housing component 340 is utilized as a stand for the roller/rotating component 330 and the closed membrane incubation component 310, as well as to house the driving means for facilitating the rotation of the closed membrane incubation component 310, such as a motor, the speed controller knob, the on/off switch, and the electronics board comprising transistor(s), resistor(s), etc., of the apparatus 300. The motor suitable for use herein may be any motor capable of running 5 rpm to 200 rpm at about 0.4 horsepower.

The pump component 350 is utilized to pump the incubation media, as well as the washing solution, in and out of the closed membrane incubation component 310. The pump component 350 comprises a pump 351, preferably a peristaltic micro pump, and a fluid transfer means 352, preferably, a tubing. The micro pump suitable for use herein may be any pump capable of delivering 200 ml to 4000 ml of volume per minute, preferably, a peristaltic MasterFlex® pump having such a capability (available from Cole-Parmer Instrument Company, Vernon Hills, Ill.) The tubing 352, comprising two opposing ends and capable of engagement with the valve 315a or 315b, is utilized for the transfer of any of the fluids used in the process, e.g., the incubation media and the washing solution, into or out of the closed incubation chamber. The tubing 352 is selected for proper fit with the pump 351 being used (e.g., sized for the pump head type and speed) and to provide proper flow of fluids therethrough. The micro pump 351 assists in the delivery of the incubation media, as well as the washing solution, to, or their removal from, the closed membrane incubation component 310 via the tubing 352 and the valve 315a or 315b.

The rotating closed-chamber membrane incubation apparatus of the present invention is designed such that all membranes can be uniformly processed, with a reduction in the use of incubation media and any harmful materials therein, due at least in part to the rotating feature and the inclusion of the mixing block. Further, the perpendicular positioning of the membranes to the rotation axis of the rolls contributes to increased immunoblotting efficiency and capacity. Moreover, this apparatus provides the advantage of enabling the safe use of radioactivity or other potentially harmful chemicals without the threat of contamination to the laboratory, as well as dramatically decreasing radioactivity handling time and human exposure. The combination of the use of the rotating closed-chamber membrane incubation apparatus and the improved two-dimensional gel electrophoresis method of the present invention allows for the processing of a 1000 patients' samples per week, making the two-dimensional biomolecules separation, particularly HDL separation, technique clinically feasible. Also, the small to medium-scale and the large-scale rotating closed-chamber membrane incubation apparatus makes any type of immunoblotting (Northern, Southern, and Western blot) on membranes very safe and effective.

Although the present invention apparatus is discussed herein mostly with respect to immunoblotting of HDL particles, it should not be construed as being restricted to HDL particles in its application, as it can be used with any type of biomolecules to process any type of immunoblot on membranes. Further, the present apparatus for immunoblotting should not be construed as being restricted to facilitating the specific technique of two-dimensional use of lipoproteins, as it can be used for any immunoblotting technique, such as Northern blotting, Southern blotting, and Western blotting.

4. Use of Gel Electrophoresis Separated and Immuno-Detected Biomolecules

The biomolecules processed via the methods and apparatus of the present invention, including but not limited to subfractionated and immunoblotted HDL particles, are useful in a variety of applications, and particularly attractive for use in a clinical setting. The ability to more accurately, specifically, and quantitatively determine biomolecules can lead to optimized therapy, as the information obtained from the resultant separated biomolecules and identification thereof can provide great insight into an individual's pathophysiological condition, which would facilitate individualized and evidence-based therapy. For example, with regard to HDL particles, two-dimensional gel electrophoresis is the only HDL separation method capable of separating the pre$\beta$-1 subclass from the $\alpha$- and pre$\alpha$-mobility HDL subclasses. This information provides a great benefit to patients with high 'pre$\beta$-1 to $\alpha$-1' ratios, as such patients have a low cholesterol ester transfer protein (CETP) and/or a low hepatic lipase (HL) function, and the therapy for both of these conditions involve a different medication than that would be appropriate for patients having conditions associated with high $\alpha$-3, '$\alpha$-4 to $\alpha$-1' ratios, or have only low $\alpha$-1 levels. Thus, the information obtained from the HDL particles, processed via the methods and apparatus of the present invention, dictates whether a patient should receive statin therapy, fibric acid therapy, or niacin therapy, respectively. The separated and immunoblotted HDL particles can be used for assessing CVD risk, evaluating efficacy of lipid medications, and optimizing personalized therapy. Details associated with the methods for use of such particles in a clinical setting can be found in the applicants' US patent application having the Ser. No. 12/472,351, which is incorporated herein by reference.

Although the use of the biomolecules processed via the methods and apparatus disclosed herein is discussed in greater detail with respect to HDL particles, any biomolecules that can be processed via the methods and apparatus of the present invention may be useful in a variety of known applications, including clinical applications, as well as facilitate the development of applications that are not currently known or not yet feasible. Such applications include, but are not limited to, determination of expression levels of the protein encoded by the targeted gene; determination of the sequence of alleles of a locus of interest; determination of mRNA concentration; and, direct genotyping.

As noted above, the present invention pertains to methods and apparatus related to separation and immuno-detection of biomolecules, as well as to the use, including use in a clinical setting, of the biomolecules processed via these methods and apparatus. The present invention should not be considered limited to the particular embodiments described above, but rather should be understood to cover all aspects of the invention as fairly set out in the appended claims. Various modifications, equivalent processes, as well as numerous structures to which the present invention may be applicable will be readily apparent to those skilled in the art, to which the present invention is directed, upon review of the present application. The claims are intended to cover such modifications.

We claim:

1. A device for immunoblotting, the device comprising:
   a plurality of incubation chambers, each comprising a body and configured to contain a plurality of membranes within the body; and
   a rotational element for rotating the incubation chamber and defining a rotational axis, wherein the incubation chamber rotates in parallel with the rotational axis.

2. The device of claim 1, wherein the rotational element comprises at least two rolls.

3. The device of claim 2, wherein the at least two rolls are parallel with the incubation chamber.

4. The device of claim 1, wherein said incubation chamber is configured to contain an incubation media.

5. The device of claim 1, wherein the incubation chamber is cylindrical in shape.

6. The device of claim 1, wherein the incubation chamber body comprises at least one opening configured to couple to a cover.

7. The device of claim 1, wherein each of the plurality of incubation chambers are operably associated with the rotational element.

8. The device of claim 1, wherein each of the plurality of incubations chambers are configured to contain a plurality of membranes.

9. The device of claim 1, wherein the plurality of membranes comprises 100 membranes or fewer.

10. The device of claim 1, wherein the incubation chamber is operably coupled to a pumping mechanism.

11. The device of claim 10, wherein the pumping mechanism is a peristaltic pump.

12. The device of claim 11, wherein the peristaltic pump is configured to deliver a fluid into and/or out of said incubation chamber.

13. The device of claim 12, wherein the fluid is selected from the group consisting of incubation media, a washing solution, and a combination thereof.

14. The device of claim 1, wherein the device is configured to perform an immunoblotting technique selected from the group consisting of a Northern blot, Southern blot, and Western blot.

15. An assembly for immunoblotting, the assembly comprising
- a plurality of incubation chambers, each incubation chamber comprising a body and configured to contain a plurality of membranes within the body; and
- a rotational element for rotating the plurality of incubation chambers and defining a rotational axis, wherein each incubation chamber rotates in parallel with the rotational axis.

16. The assembly of claim 15, wherein the rotational element comprises at least two rolls.

17. The assembly of claim 16, wherein the at least two rolls are parallel with the plurality of incubation chambers.

18. The assembly of claim 15, wherein the plurality of incubation chambers is operably coupled to a pumping mechanism.

19. The assembly of claim 18, wherein the pumping mechanism comprises a peristaltic pump configured to deliver a fluid into and/or out of the incubation chamber.

* * * * *